US006743598B2

(12) United States Patent
Selitrennikoff et al.

(10) Patent No.: US 6,743,598 B2
(45) Date of Patent: Jun. 1, 2004

(54) METHODS FOR THE IDENTIFICATION OF FUNGAL GLUCOSE UTILIZATION INHIBITORS AND ANTIFUNGAL AGENTS

(75) Inventors: Claude P. Selitrennikoff, Evergreen, CO (US); Mitsunori Nakata, Denver, CO (US)

(73) Assignees: MycoLogics, Inc., Denver, CO (US); Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/927,734

(22) Filed: Aug. 10, 2001

(65) Prior Publication Data

US 2003/0194758 A1 Oct. 16, 2003

(51) Int. Cl.$^7$ .............................. C12Q 1/54; C12Q 9/58
(52) U.S. Cl. ......................... 435/14; 435/233; 424/725; 424/780; 424/195.17
(58) Field of Search .................. 435/14, 233; 424/725, 424/195.17, 780

(56) References Cited

U.S. PATENT DOCUMENTS 5,945,315 A  *  8/1999  Moore et al. ................ 435/106
6,346,252 B1 *  2/2002  Moigne ................... 424/195.17

FOREIGN PATENT DOCUMENTS

WO        WO 98/10656      *  3/1998

OTHER PUBLICATIONS

Marchand et al, Eur. J. Biochem. 184:455–464 (1989).*
Anaissie, "Opportunistic mycoses in the immunocompromised host: experience at a cancer center and review," *Clin. Infect. Dis.*, 14(Suppl 1):S43–S53 [1992].
Badet et al., "Glucosamine synthetase from *Escherichia coli*: Purification, properties, and glutamine–utilizing site location," *Biochemistry* 26:1940–1948 [1987].
Beck–Sague et al.,"Secular trends in the epidemiology of nosocomial fungal infections in the United States, 1980–1990," *J. Infect. Dis.*, 167:1247–1251 [1993].
Boehmelt et al., "Cloning and characterization of the murine glucosamine–6–phosphate acetyltransferase EMeg32,"*J. Biol. Chem.* 275:12821–12832 [2000].
Borgia, "Roles of the orlA, tsE, and blmG genes of *Aspergillus nidulans* in chitin synthesis," *J. Bacteriol.*, 174:384–3898 [1992].
Boschman et al., "Thirteen–year evolution of azole resistance in yeast isolates and prevalence of resistant strains carried by cancer patients at a large medical center," *Antimicrob. Agents Chemother.*, 42:734–738 [1998].
Bow, "Invasive fungal infections in patients receiving intensive cytotoxic therapy for cancer," *Br. J. Haematol.*, 101(Suppl 1):1–4 [1998].
Bulawa, "Genetics and molecular biology of chitin synthesis in fungi,"*Annu. Rev. Microbiol.*, 47:505–534 [1993].

Clifton et al., "Glycolysis mutants in *Saccharomyces cerevisiae*," *Genetics* 88:1–11 [1978].
Cole, "Basic biology of fungi," in Baron (ed.) *Medical Microbiology*, 4th edition, (Galveston, TX: University of Texas Medical Branch) pp. 903–911 [1996].
Cox and Perfect, "Fungal infections," *Curr. Opin. Infect. Dis.* 6:422–426 [1993].
Datta et al., "Current trends in *Candida albicans* research," *Adv. Microb. Physiol.* 30:53–88 [1989].
Decker et al., "Structure–activity relationships of the nikkomycins," *J. Gen. Microbiol.*, 137:1805–1813 [1991].
Denning et al., "Pulmonary aspergillosis in the acquired immunodeficiency syndrome," *New Eng. J. Med.*, 324:654–662 [1992].
Dixon and Walsh, "Antifungal Agents," In Baron (ed.) *Medical Microbiology*, 4th edition, (Galveston, TX: University of Texas Medical Branch) pp. 926–932 [1996].
Endo et al., "Feedback inhibition of L–glutamine D–fructose 6–phosphate amidotransferase by uridine diphosphate N–acetylglucosamine in *Neurospora crassa*," *J. Bacteriol.*, 103:588–594 [1970].
Etechebehere and Da Costa Maia, "Phosphorylation–dependent regulation of amidotransferase during development of *Blastocladiella emersonii*," *Arch. Biochem. Biophys.*, 272:301–310 [1989].
Etchebehere et al., "Development regulation of hexasomine biosynthesis by protein phosphatases 2A and 2C in *Blasiocladiella emersonii*," *J. Bacteriol.*, 175:5022–5027 [1993].
Fox, "Fungal infection rates are increasing," *ASM News* 59:515–518 [1993].
Goodwin et al., "A nationwide survey of clinical laboratory methodologies for fungal infections," *J. Med. Vet. Mycol.*, 30:153–160 [1992].
Gopal et al., "Enzymes of N–acetylglucosamine metabolism during germ–tube formation in *Candida albicans*," *J. Gen. Microbiol.* 128:2319–2326 [1982].
Graybill, "The future of antifungal therapy," *Clin. Infect. Dis.*, 22(Suppl 2):S166–S178 [1996].
Hardre et al., "Competitive inhibition of *Trypanosoma brucei* phosphoglucose isomerase by D–arabinose–5–phosphate derivatives," *J. Enzyme Inhib.* 15:509–515 [2000].
Herrera and Pascal, "Genetical and biochemical studies of glucosephosphate isomerase deficient mutants in *Saccharomyces cerevisiae*," *J. Gen. Microbiol.* 103:305–310 [1978].
Katz and Rosenberger, "A mutation in *Aspergillus nidulans* producing hyphal walls which lack chitin," *Biochim. Biophys. Acta.*, 208:452–460 [1970].

(List continued on next page.)

Primary Examiner—Francisco Prats
(74) Attorney, Agent, or Firm—Medlen & Carroll LLP

(57) ABSTRACT

The present invention provides methods for simultaneously assessing microbial phosphoglucose isomerase, ketolisomerase and glucosamine-6-phosphate acetyltransferase activities, by measuring the production of Coenzyme A (CoA). The present invention finds use in the isolation of new classes of antifungal drugs, wherein the compounds have the ability to inhibit fungal glucose utilization.

12 Claims, 5 Drawing Sheets

OTHER PUBLICATIONS

Leloir and Cardini, "The biosynthesis of glucosamine," *Biochim. Biophys. Acta.*, 12:15–22 [1953].
Lipke and Ovalle, "Cell wall architecture in yeast: New structure and new challenges," *J. Bacteriol.* 185:3735–3740 [1998].
Lortholary et al., "Invasive aspergillosis in patients with acquired immunodeficiency syndrome: report of 33 cases," *Amer. J. Med.*, 95:177–187 [1993].
Marchand et al., "Glucosephosphate isomerase from *Trypanosoma brucei*," *Eur. J. Biochem.* 184:455–464 [1989].
McCullough, "Importance of chitin synthesis for fungal growth and as a target for antifungal agents," In Fernandes (ed.), *New Approaches for Antifungal Drugs* (Boston : Birkhauser) pp. 32–45 [1992].
McGinnis and Tyring, "Introduction to Mycology," In Baron (ed.), *Medical Microbiology*, 4th edition, (Galveston TX: University of Texas Medical Branch) pp. 893–902 [1996].
McKnight et al.; "Molecular cloning, cDNA sequence, and bacterial expression of human glutamine:fructose–6–phosphate amidotransferase," *J . Biol. Chem.*, 267:25208–25212 [1992].
Mellado et al., "A multigene family related to chitin synthase genes of yeast in the opportunistic pathogen *Aspergillus fumigatus.*" *Mol. Gen. Genet.*, 246:353–359 [1995].
Meng et al., "Probing the location and function of the conserved histidine residue of phosphoglucose isomerase by using an active site directed inhibitor N–bromoacetylethanolamine phosphate," *Protein Sci.* 8:2438–2443 [1999].
Meunier, et al., "Candidemia in immunocompromised patients," *Clin. Infect. Dis.*, 14(Suppl 1):S120–S125 [1992].
Milewski et al., "Mechanism of action of anticandidal dipeptides containing inhibitors of glucosamine–6–phosphate synthase," *Antimicrob. Agents Chem.*, 35:36–43 [1991].
Miller et al., "Pulmonary aspergillosis in patients with AIDS," *Chest* 105:37–44 [1994].
Mio et al., "Role of three chitin synthase genes in the growth of *Candida albicans,*" *J. Bacteriol.* 178:2416–2419 [1996].
Mio et al., "*Saccharomyces cerevisiae* GNA1, an essential gene encoding a novel acetyltransferase involved in UDP-N–acetylglucosamaine synthesis," *J. Biol. Chem.* 274:424–429 [1999].
Mio et al., "Reduced virulence of *Candida albicans* mutants lacking the GNA1 gene encoding glucosamine–6–phosphate acetylftransferase," *Microbiology* 146:1753–1758 [2000].
Mitchell, "Opportunistic mycoses," In Joklik et al. [eds], Zinsser Microbiology, (Norwald, CT: Appleton, Century-Crofts) pp. 1183–1197 [1984].
Monks et al., "Feasibility of a high–flux anticancer drug screen using a diverse panel of cultured human tumor cell lines," *J Natl Cancer Inst* 83:757–766 [1991].
Navon et al., "Phosphorus–31 nuclear magnetic resonance studies of wild type and glycolytic pathway mutants of *Saccharomyces cerevisiae,*" *Biochemistry* 18:4487–4499 [1979].
Noltmann, "Phosphoglucose isomerase," *Methods Enzymol.* 9:557–565 [1966].
Polis and Kovacs, "Fungal Infections in Patients with the Acquired Immunodeficiency Syndrome," in DeVita et al. (eds), *AIDS: Biology, Diagnosis, Treatment, and Prevention*, 4th ed., (Philadelphia, PA: Lippincott–Raven Publishers) pp. 231–244 [1997].
Riddles et al., "Reassessment of Ellman's reagent," *Methods Enymol.* 91:49–61 [1983].
Russell and Srb, "A study of L–glutamine:D–fructose 6–phosphate amidotransferase in certain developmental mutants of *Neurospora crassa,*" *Molec. Gen. Genet.*, 129:77–86 [1974].
Selitrennikoff and Ostroff, "Emerging therapeutic cell wall targets in fungal infections," *Emerging Therapeutic Targets* 3:53–72 [1999].
Selitrennikoff and Sonneborn, "Post–translational control of de Novo cell wall formation during *Blastocladiella emersonii* zoospore germination,"*Develop. Biol.*, 54:37–51 [1976].
Selitrennikoff and Sonneborn, "The last two pathway–specific enzyme activities of hexosamine biosynthesis are present in *Blastocladiella emersonii* zoospores prior to germination," *Biochim. Biophys. Acta.*, 451:408–416 [1976].
Sheehan, "Current and emerging azole antifungal agents,"*Clin. Microbiol. Rev.* 12:40–79 [1999].
Singh and Datta, "Induction of N–acetylglucosamine–catabolic pathway is spheroplasts of *Candida albicans,*" *Biochem. J.* 178:427–431 [1979].
Sigler and Kennedy, "Aspergillus, Fusarium, and other opportunistic moniliaceous fungi," In Murray et al. (eds.), *Manual of Clinical Microbiology,* 7th edition, (Washington DC: ASM Press) pp. 1213–1241 [1999].
Smith et al., "Isolation and characterization of the GFA1 gene encoding the glutamine:fructose–6–phosphate amidotransferase of *Candida albicans,*" *J. Bacteriol.*, 178:2320–2327 [1996].
Smits et al., "Cell wall dynamics in yeast," *Curr. Opin. Microbiol.* 2:348–352 [1999].
Sun et al., "The crystal structure of a multifunctional protein: Phosphoglucose isomerase/autocrine motility factor/neuroleukin,"*Proc. Natl. Acad. Sci. USA* 96:5412–5417 [1999].
Tokomura and Horie, "Kinetics of nikkomycin Z degradation in aqueous solution and in plasma," *Biol. Pharm. Bull.*, 20:577–580 [1997].
Walsh and Dixon, "Spectrum of mycoses," In Baron (ed.), *Medical Microbiology,* 4th edition, (Galveston: TX: University of Texas Medical Branch) pp. 919–925 [1996].
Warnock, "Fungal infections in neutropenia: current problems and chemotherapeutic control," *J. Antimicrob. Chemother.*, 41:95–105 [1998].
Warren and Hazen, "Candida, Cryptococcus, and other yeasts of medical importance," In Murray et al. (eds.), *Manual of Clinical Microbiology,* 7th edition, (Washington, DC: ASM Press) pp. 1184–1199 [1999].
Watzele and Tanner, "Cloning of the glutamine:fructose–6–phosphate amidotransferase gene from yeast," *J. Biol. Chem.*, 264:8753–8758 [1989].
White, "Antifungal drug resistance in *Candida albicans,*" *ASM News* 63:427–433 [1997].
White et al., "Clinical, cellular, and molecular factors that contribute to antifungal drug resistance," *Clin. Microbiol. Rev.*, 11:382–402 [1998].
Winterburn and Phelps, "Purification and some kinetic properties of rat liver glucosamine synthetase," *Biochem. J.*, 121:701–709 [1971].
Zalkin, "Glucosamine–6–phosphate synthase," *Methods Enzymol.*, 113:278–281 [1985].
Zhou et al., "Regulation of glutamine:fructose–6–phosphate amidotransferase by cAMP–dependent protein kinase," *Diabetes* 47:1836–1840 [1998].
GenBank™ accession No. AF185571.
GenBank™ accession No. U40369.
GenBank™ accession No. X14672.
http://dtp.nci.nih.gov/docs/compare/compare%5Fmethodology.html.

\* cited by examiner

SEQUENCE LISTING

<160> NUMBER OF SEQ ID NOS: 14

<210> SEQ ID NO 1
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Xaa at this position can be Val, Ile, or Leu.
<220> FEATURE:
<221> NAME/KEY: SITE
<222> LOCATION: (4)..(6)
<223> OTHER INFORMATION: Xaa at these positions can be Val, Ile, or Leu.
<220> FEATURE:
<221> NAME/KEY: SITE
<222> LOCATION: (7)..(9)
<223> OTHER INFORMATION: Xaa at these positions can be any amino acid.
<220> FEATURE:
<221> NAME/KEY: SITE
<222> LOCATION: (10)..(10)
<223> OTHER INFORMATION: Xaa at thIs position can be Val, Ile, or Leu.
<220> FEATURE:
<221> NAME/KEY: SITE
<222> LOCATION: (13)..(13)
<223> OTHER INFORMATION: Xaa at this position can be any amino acid.
<220> FEATURE:
<221> NAME/KEY: SITE
<222> LOCATION: (15)..(15)
<223> OTHER INFORMATION: Xaa at this position can be Val, Ile, or Leu.
<220> FEATURE:
<221> NAME/KEY: SITE
<222> LOCATION: (17)..(17)
<223> OTHER INFORMATION: Xaa at this position can be Ser or Thr.
<220> FEATURE:
<221> NAME/KEY: SITE
<222> LOCATION: (18)..(18)
<223> OTHER INFORMATION: Xaa at this position can be any amino acid.
<220> FEATURE:
<221> NAME/KEY: SITE
<222> LOCATION: (19)..(20)
<223> OTHER INFORMATION: Xaa at these positions can be Val, Ile, or Leu.

<400> SEQUENCE: 1

Xaa Glu Asp Xaa Xaa Xaa Xaa Xaa Xaa Xaa Arg Gly Xaa Gly Xaa Gly
1               5                   10                  15

Xaa Xaa Xaa Xaa
            20

<210> SEQ ID NO 2
<211> LENGTH: 13
<212> TYPE: PRT
<213> ORGANISM: Artificial Sequence
<220> FEATURE:
<223> OTHER INFORMATION: Synthetic

```
<220> FEATURE:
<221> NAME/KEY: SITE
<222> LOCATION: (2)..(2)
<223> OTHER INFORMATION: Xaa at this position can be any amino acid.
<220> FEATURE:
<221> NAME/KEY: SITE
<222> LOCATION: (5)..(5)
<223> OTHER INFORMATION: Xaa at this position can be Val, Ile, or Leu.
<220> FEATURE:
<221> NAME/KEY: SITE
<222> LOCATION: (6)..(6)
<223> OTHER INFORMATION: Xaa at this position can be any amino acid.
<220> FEATURE:
<221> NAME/KEY: SITE
<222> LOCATION: (7)..(7)
<223> OTHER INFORMATION: Xaa at this position can be Val, Ile, or Leu.
<220> FEATURE:
<221> NAME/KEY: SITE
<222> LOCATION: (9)..(9)
<223> OTHER INFORMATION: Xaa at this position can be any amino acid.
<220> FEATURE:
<221> NAME/KEY: SITE
<222> LOCATION: (10)..(10)
<223> OTHER INFORMATION: Xaa at this position can be Lys, Arg, or His.
<220> FEATURE:
<221> NAME/KEY: SITE
<222> LOCATION: (11)..(11)
<223> OTHER INFORMATION: Xaa at this position can be Val, Ile, or Leu.
<220> FEATURE:
<221> NAME/KEY: SITE
<222> LOCATION: (13)..(13)
<223> OTHER INFORMATION: Xaa at this position can be Tyr or Phe.

<400> SEQUENCE: 2

Asn Xaa Pro Ala Xaa Xaa Xaa Tyr Xaa Xaa Xaa Gly Xaa
1               5                   10

<210> SEQ ID NO 3
<211> LENGTH: 20
<212> TYPE: PRT
<213> ORGANISM: Candida albicans

<400> SEQUENCE: 3

Ile Glu Asp Ile Ser Val Ala Lys Ser Glu Gln Gly Lys Lys Leu Gly
1               5                   10                  15

Tyr Tyr Leu Val
            20

<210> SEQ ID NO 4
<211> LENGTH: 10
<212> TYPE: PRT
<213> ORGANISM: Candida albicans

<400> SEQUENCE: 4

Asn Val Gly Phe Tyr Glu Lys Cys Gly Tyr
1               5                   10

<210> SEQ ID NO 5
<211> LENGTH: 23
<212> TYPE: PRT
<213> ORGANISM: Saccharomyces cerevisiae

<400> SEQUENCE: 5

Ile Glu Asp Ile Ala Val Asn Ser Lys Tyr Gln Gly Gln Gly Leu Gly
1               5                   10                  15

Lys Leu Leu Ile Pro Arg Thr
            20

<210> SEQ ID NO 6
```

```
<211> LENGTH: 10
<212> TYPE: PRT
<213> ORGANISM: Saccharomyces cerevisiae

<400> SEQUENCE: 6

Asn Val Lys Phe Tyr Glu Lys Cys Gly Phe
1               5                   10

<210> SEQ ID NO 7
<211> LENGTH: 20
<212> TYPE: PRT
<213> ORGANISM: Mus musculus

<400> SEQUENCE: 7

Val Glu Asp Val Val Val Ser Asp Glu Cys Arg Gly Lys Gln Leu Gly
1               5                   10                  15
Lys Leu Leu Leu
            20

<210> SEQ ID NO 8
<211> LENGTH: 10
<212> TYPE: PRT
<213> ORGANISM: Mus musculus

<400> SEQUENCE: 8

Asn Val Gly Phe Tyr Lys Lys Phe Asp Tyr
1               5                   10

<210> SEQ ID NO 9
<211> LENGTH: 20
<212> TYPE: PRT
<213> ORGANISM: Homo sapiens

<400> SEQUENCE: 9

Leu Glu Asp Phe Phe Val Met Ser Asp Tyr Arg Gly Phe Gly Ile Gly
1               5                   10                  15
Ser Glu Ile Leu
            20

<210> SEQ ID NO 10
<211> LENGTH: 13
<212> TYPE: PRT
<213> ORGANISM: Homo sapiens

<400> SEQUENCE: 10

Asn Glu Pro Ser Ile Asn Phe Tyr Lys Arg Arg Gly Ala
1               5                   10

<210> SEQ ID NO 11
<211> LENGTH: 20
<212> TYPE: PRT
<213> ORGANISM: Homo sapiens

<400> SEQUENCE: 11

Tyr Ser Thr Gly Met Val His Leu Leu Leu Gln Val Thr Ile Asp Gly
1               5                   10                  15
Arg Asn Tyr Ile
            20

<210> SEQ ID NO 12
<211> LENGTH: 10
<212> TYPE: PRT
<213> ORGANISM: Homo sapiens

<400> SEQUENCE: 12
```

```
Ile Glu Ala Tyr Phe Glu Arg Ile Gly Tyr
1               5                   10
```

<210> SEQ ID NO 13
<211> LENGTH: 20
<212> TYPE: PRT
<213> ORGANISM: Homo sapiens

<400> SEQUENCE: 13

```
Leu Phe His Leu Ser Val Asp Asn Glu His Arg Gly Gln Gly Ile Ala
1               5                   10                  15

Lys Ala Leu Val
            20
```

<210> SEQ ID NO 14
<211> LENGTH: 13
<212> TYPE: PRT
<213> ORGANISM: Homo sapiens

<400> SEQUENCE: 14

```
Gln Leu Ser Ala Met Gly Leu Tyr Gln Ser Leu Gly Phe
1               5                   10
```

METHODS FOR THE IDENTIFICATION OF FUNGAL GLUCOSE UTILIZATION INHIBITORS AND ANTIFUNGAL AGENTS

FIELD OF THE INVENTION

The present invention provides methods for simultaneously assessing microbial phosphoglucose isomerase, ketol-isomerase and glucosamine-6-phosphate acetyltransferase activities, by measuring the production of Coenzyme A (CoA). The present invention finds use in the isolation of new classes of antifungal drugs, wherein the compounds have the ability to inhibit fungal glucose utilization.

BACKGROUND OF THE INVENTION

During the last three decades there has been a dramatic increase in the frequency of fungal infections, especially disseminated systemic mycoses in immunocompromised patients (Cox and Perfect, *Curr. Opin. Infect. Dis.* 6:422–426 [1993]; and Fox, *ASM News* 59:515–518 [1993]). Human pathogenic fungi of particular importance include: *Candida sp.* (*C. albicans, C. glabrata, C. krusei* and *C. parapsilosis*), *Aspergillus fumigatus*, and *Cryptococcus neoformans*. *C. albicans* and *A. fumigatus* cause most opportunistic mycoses. At present, treatments for fungal infections are limited to few options. Amphotericin B (a polyene) is fungicidal, but is toxic to humans. Azoles (fluconazole, itraconazole, and others) are safer than amphotericin B, but are only fungistatic. In addition, resistance to azoles has become a major clinical concern. Some azoles (Sheehan, *Clin. Microbiol. Rev.* 12:40–79 [1999]) and a new class of (1,3)β-glucan synthase inhibitors, echinocandins (Denning, *J. Antimicrob. Chemother.* 40:611–614 [1997]), are now in clinical and pre-clinical trials. Recently, the FDA approved caspofungin, a (1,3)β-glucan synthase inhibitor, as a "salvage treatment" for aspergillosis. In spite of the new azoles and the (1,3)β-glucan synthase inhibitors, new classes of antifungal drugs are needed for therapy of infections caused by drug-resistant mutants (and species) or for preventing the emergence of drug-resistant mutants.

Fungal Infections and Drug Resistance

Fungal organisms have become increasingly significant pathogens in immunocompromised patients, especially those who because of cancer, organ transplantation, chemotherapy, pregnancy, age, diabetes, complications following extensive surgery, and various immune system dysfunctions, are at risk of experiencing life-threatening diseases caused by microorganisms which do not ordinarily pose a threat to normal, immunocompetent people. Other risk factors for deeply invasive fungal infections include protracted treatment using broad spectrum antimicrobials, corticosteroids, and vascular catheters.

Indeed, immunocompromised patients provide a significant challenge to modern health care delivery. For example, fungal infections have become one of the leading factors contributing to morbidity and mortality in cancer patients, and fungi account for 4–12% of nosocomial pathogens in leukemia patients (Anaissie, *Clin. Infect. Dis.*, 14[Suppl. 1]:S43 [1992]). The incidence of nosocomial bloodstream infections with fungi such as Candida spp. ("candidemia") has increased in recent years and has been reported to account for 5.6% of all primary bloodstream infections. There are an estimated 200,000 patients/year who acquire nosocomial fungal infections, with bloodstream infections having a mean mortality rate of 55% (See e.g., Beck-Sague et al., *J. Infect. Dis.*, 167:1247 [1993]; and the Centers for Disease Control website at www.cdc.gov/ncidod/publications/brochures/hip.html). Fungal infections in non-humans, such as livestock, is also of significant health and economic concern. The most common fungal pathogens in humans are the opportunistic yeast, *Candida albicans* and the filamentous mold, *Aspergillus fumigatus* (See, Bow, *Br. J. Haematol.*, 101:1 [1998]; and Warnock, *J. Antimicrob. Chemother.*, 41:95 [1998]).

*C. albicans* is the most common fungal pathogen in humans, with other Candida species becoming increasingly important in fungal disease in humans and other animals (See, Walsh and Dixon, "Spectrum of Mycoses," in Baron [ed.], *Medical Microbiology*, 4th ed, University of Texas Medical Branch, Galveston, Tex. [1996], pp. 919–925). Approximately 200 Candida species are recognized, with approximately seven of those species isolated with significant frequency from human specimens (See, Warren and Hazen, Ch. 95, pp. 1184–1199, "Candida, Cryptococcus, and Other Yeasts of Medical Importance," in Murray et al., [eds.], *Manual of Clinical Microbiology*, 7th ed., ASM Press, Washington, D.C. [1999]; and Mitchell, in *Zinsser Microbiology*, Joklik et al., [eds], Appleton, Century-Crofts, Norwalk, Conn., pp. 1183–1190 [1984]).

The clinical manifestations of Candida infections and disease are many and varied, as Candida species are known to invade most organ systems of the body. Superficial candidiasis may involve the epidermal and mucosal surfaces (e.g., the oral cavity, pharynx, esophagus, intestines, urinary bladder, and vagina). In deep candidiasis, the gastrointestinal tract and intravascular catheters are the two major portals of entry, with the kidneys, liver, spleen, brain, eyes, heart, and other tissues being the major sites involved.

The major difficulties in treating Candida infections are encountered in cases of systemic disease. Chronic mucocutaneous, pulmonary candidiasis, endocarditis, and fungemia must be diagnosed early in order to avoid fatality. The incidence of candidiasis in certain patient populations is striking. Up to 30% of leukemia patients acquire systemic candidiasis (Anaissie, *Clin. Infect. Dis.*, 14[Suppl. 1]:S43 [1992]). This is of great significance, as some reports indicate that the fatality rate for disseminated candidiasis in cancer patients is as high as 80% (Meunier, et al., *Clin. Infect. Dis.*, 14[Suppl. 1]:S120 [1992]).

Aspergillus species are the second most common isolate, after Candida species, in patients with positive fungal cultures (See, Sigler and Kennedy, Ch. 97, "Aspergillus, Fusarium, and Other Opportunistic Moniliaceous Fungi," in Murray et al., (eds), *Manual of Clinical Microbiology*, 7th ed., ASM Press, Washington, D.C. [1999], pp. 1213–1241; and Goodwin et al., *J. Med. Vet. Mycol.*, 30:153 [1992]). A large number of species of the genus Aspergillus have clinical relevance, although *A. fumigatus*, *A. niger* and *A. flavus* are most commonly isolated. Of these isolates, *A. fumigatus* is the most common human pathogen. Three main types of disease have been associated with *A. fumigatus*, namely allergic asthma, aspergilloma, and invasive aspergillosis (See e.g., Lortholary et al., *Amer. J. Med.*, 95:177–187 [1993]).

Allergic pulmonary asthma due to *A. fumigatus* exposure affects an estimated 50,000 individuals in the United States alone. Aspergillomas are formed when fungal spores germinate in situ in tissue such as the lungs and form fungus balls. There is typically no invasion of underlying tissues, and in most cases treatment involves the simple surgical removal of the aspergilloma. However, invasive aspergillosis involves the invasion of host tissues, and is most commonly observed in patients with predisposing conditions (e.g., immunosuppressive drugs, neutropenia, chemotherapy, AIDS). Transplant (e.g., bone marrow or organ) and chemotherapy patients are at the greatest risk for this form of aspergillosis (See e.g., Denning et al., *New Eng. J. Med.*, 324:654–662 [1992]; and Miller et al., *Chest* 105:37–44 [1994]). The prognosis for patients with invasive aspergillosis is particularly grave, with mortality rates greater than 50% (See e.g., Polis et al., "Fungal Infections in Patients with the Acquired Immunodeficiency Syndrome," in DeVita et al. (eds), *AIDS: Biology, Diagnosis, Treatment, and Prevention*, 4th ed., Lippincott-Raven, [1997]), due to the lack of a rapid diagnostic method to confirm *A. fumigatus* infection, and the lack of safe antifungal drugs.

The development of effective antifungal agents has lagged behind that of antibacterial agents. Fungi, like humans, are eukaryotic. Thus, most agents that have antimicrobial activity towards fungi are also toxic to humans (i.e., due to non-selective toxicity). Four general groups of antifungals have been developed; these are the polyenes, the azoles, the allylamines/morpholines, and the antimetabolites. Despite the identification of cell membrane, cell wall, and microtubule targets for antifungal action, antifungal development has been slow.

The polyene antifungals (e.g., amphotericin B and nystatin) target the fungal cell membrane, which is similar to mammalian plasma membranes, with the exception being that fungal plasma membranes contain ergosterol, rather than cholesterol as the principal sterol. The polyene amphotericin B remains the treatment mainstay for life-threatening and other mycoses, including candidiasis, cryptococcosis, aspergillosis, zygomycosis, coccidioidomycosis, histoplasmosis, blastomycosis, and paracoccidioidomycosis. Amphotericin B must be administered intravenously and is associated with numerous, often serious side effects, including phlebitis at the infusion site, fever, chills, hypokalemia, anemia and nephrotoxicity. Nystatin is another broad-spectrum polyene antifungal. However, its toxicity to humans prevents its widespread use. Currently, it is limited to topical applications, where it is effective against yeasts, including *C. albicans*.

The azole antifungals (e.g., fluconazole, itraconazole, and ketoconazole) and the allylamine and morpholine antifungals (e.g., naftifine and terbinafine) interfere with ergosterol biosynthesis. Ketoconazole may be used to treat histoplasmosis, blastomycosis, mucosal candidiasis and various cutaneous mycoses (e.g., dermatophyte infections, pityriasis versicolor, and cutaneous candidiasis). However, it is not useful for treatment of aspergillosis or systemic yeast infections. Side effects associated with use of the azoles are not as severe as those associated with amphotericin B, although life-threatening hepatic toxicity may result from long-term azole use. Other side effects include nausea, vomiting, and drug interactions with such compounds as cyclosporin, antihistamines, anticoagulants, anti-seizure and oral hypoglycemic medications.

The few antimetabolite antifungals identified have not found widespread use. The most commonly used antifungal is 5-fluorocytosine, a fluorinated analog of cytosine. However, as with other antimetabolites, drug resistant fungal strains have emerged, and 5-fluorocytosine is seldom used alone. Nonetheless, in combination with amphotericin B, it remains the treatment of choice for cryptococcal meningitis, and is effective against some diseases caused by dematiaceous fungi.

Griseofulvin, an antifungal compound produced by *Penicillium griseofulvin*, acts by targeting microtubule-associated proteins. Griseofulvin is active against most dermatophytes, and is commonly used to treat dermatophytic infections. Potassium iodide is another compound that is used as an antifungal to enhance transepidermal elimination of fungal organisms in cases of cutaneous and lymphocutaneous sporotrichosis, although it is not effective against *Sporothrix schenckii* in vitro.

As with bacteria, drug-resistant strains of fungal pathogens have also been reported. This drug resistance can take various forms, such as primary resistance, where the susceptibility profiles for the species are characteristic, inherent, and rarely change in response to drug exposure, or the resistance can be secondary (i.e., acquired). Some of the molecular and cellular mechanisms by which fungal organisms acquire resistance are known (White, *ASM News* 63:427–433 [1997]; and White et al., *Clin. Microbiol. Rev.*, 11:382–402 [1998]).

Significantly, fungal resistance to amphotericin B has been reported for various opportunistic fungi, including *Pseudallescheria boydii*, Fusarium, Trichosporon, and some *C. lusitaniae* and *C. guilliermondii* isolates (See, Dixon and Walsh, "Antifungal Agents," in Baron (ed.), *Medical Microbiology*, 4th ed., University of Texas Medical Branch, Galveston, Tex. [1996], pp. 926–932). In addition, the emergence of azole-resistant fungal strains has raised concerns regarding use of the azole compounds, especially fluconazole, as a front-line treatment (Boschman et al., *Antimicrob. Agents Chemother.*, 42:734 [1998]; Graybill, *Clin. Infect. Dis.*, 22(Suppl. 2):S166 [1996]; White, *ASM News* 63:427–433 [1997]; and White et al., *Clin. Microbiol. Rev.*, 11:382–402 [1998]).

In view of the development of resistance, as well as the relative lack of variety available in the selection of antifungals, there remains a need for the development of compounds useful for treatment of fungal diseases.

Selective Toxicity

The principle of selective toxicity is fundamental to the development of successful antimicrobial agents. That is to say, an antimicrobial compound, while toxic to the microorganism, ideally is not toxic to the subject receiving the antimicrobial compound. Selective toxicity is often a reflection of differences between the microorganism and host physiologies.

One approach to achieving selective toxicity is to identify a compound that is able to inhibit an essential enzyme in the microorganism, but due to differences in enzyme structure or function, that same antimicrobial compound does not affect the homologous enzyme in the host. Alternatively, an antimicrobial compound can inhibit a biochemical event that is essential to the microorganism, but that biochemical process may not be present or be essential to the host.

Chitin Biosynthesis

The fungal cell wall is essential for the viability of the organism, and is a rigid, stratified structure consisting of chitinous microfibrils and polysaccharides, among other components. The cell wall provides support and shape to the cell, and prevents osmotic lysis of the cell. Indeed, even a small lesion within the cell wall can lead to the extrusion of cytoplasm due to the positive intracellular pressure (See, Cole, "Basic Biology of Fungi, in Baron (ed.), *Medical Microbiology*, 4th ed., University of Texas Medical Branch, Galveston, Tex. [1996], pp. 903–911). The yeast form of the *C. albicans* cell wall contains approximately 30–60% glucan, 25–50% mannan (mannoprotein), 1–2% chitin, 2–14% lipid, and 5–15% protein (McGinnis and Tyring, "Introduction to Mycology," in Baron (ed.), *Medical Microbiology*, 4th ed., University of Texas Medical Branch, Galveston, Tex. [1996], pp. 893–902). The chitin within the fungal cell wall is a (1–4)β-linked polymer of N-acetyl glucosamine (GlcNAc) polymerized by chitin synthase at the plasma membrane (See, FIG. 1).

Chitin, although a minor component of yeast and filamentous fungal cell walls, is essential for cell viability and mother-daughter cell separation. Chitin biosynthesis, which requires uridine diphosphate-N-acetyl glucosamine (UDP-GlcNAc), is complex and is catalyzed by at least three gene products in S. cerevisiae, and perhaps as many as six gene products in certain filamentous molds (Bulawa, *Ann. Rev. Microbiol.*, 47:505–534 [1993]; and Mellado et al., *Mol. Genet.*, 246:353–359 [1995]). The three yeast genes, csI, csII and csIII, each have homologues in C. albicans and each performs a different intracellular function.

UDP-GlcNAc is the substrate for chitin synthase. Normal levels of UDP-GlcNAc are required for chitin biosynthesis and subsequent cell wall assembly and growth (Katz and Rosenberger, *Biochim. Biophys. Acta.*, 208:452–460 [1970]). The pathway for the synthesis of UDP-GlcNAc, known as the Leloir pathway (Leloir and Cardini, *Biochim. Biophys. Acta.*, 12:15–22 [1953]) is shown in FIG. 1. In this Figure, chitin synthase activity is shown for context, but is not considered part of the Leloir pathway. The first pathway-specific enzyme is 2-amino-2-deoxy-D-glucose-6-phosphate ketol-isomerase (known simply as ketol-isomerase; E.C. 5.3.1.19 or E.C. 2.6.1.16). The ketol-isomerase is an amino transferase that forms glucosamine-6-phosphate (GlcN-6-P) and glutamate from fructose-6-phosphate and glutamine (Selitrennikoff and Sonneborn, *Develop. Biol.*, 54:37–51 [1976]). The second enzyme in the pathway is aminodeoxyglucosephosphate acetyltransferase (E.C. 2.4.1.4), which converts S-acetyl CoA and GlcN-6-P to CoA and N-acetylglucosamine-6-phosphate (GlcNAc-6-P) (Selitrennikoff and Sonneborn, *Develop. Biol.*, 54:37–51 [1976]). The third enzyme is acetylaminodeoxyglucose phosphomutase (also known as GlcNAc-phosphomutase; E.C. 2.7.5.2) which converts GlcNAc-6-P to GlcNAc-1-phosphate, employing Glc-1,6-phosphate as a co-factor. The most downstream enzyme is UTP:acetylaminodeoxyglucose-1-phosphate uridylyl transferase (E.C. 2.7.7.23), which converts UTP and GlcNAc-1-phosphate to UDP-GlcNAc and pyrophosphate ($PP_i$) (Selitrennikoff and Sonneborn, *Biochim. Biophys. Acta.*, 451:408–416 [1976]; and Etchebehere et al., *J. Bacteriol.*, 175:5022–5027 [1993]).

Chitin synthase has been a target for the identification of antifungal compounds for over 30 years, yet only two classes of compounds that target this enzyme have been identified. These are the competitive substrate inhibitors, namely the polyoxins and the nikkomycins. Each of these enzymatic inhibitors resembles the structure of the substrate, UDP-GlcNAc, and has inhibition constants ($K_i$) in the $\mu$M range (Decker et al., *J. Gen. Microbiol.*, 137:1805–1813 [1991]). Unfortunately, nikkomycin shows rapid degradation in biological fluids in rat, mouse and rabbit model systems (Tokumura and Horie, *Biol. Pharm. Bull.*, 20:577–580 [1977]).

Thus, there remains a need to identify new antifungal compounds, and more specifically, there is a need to identify new classes of antifungal compounds that are effective against various fungal organisms, including those that are resistant to currently used compounds. Indeed, there remains a need to identify and develop new classes of antimicrobial compounds that are effective against multiple-drug resistant organisms. In addition, there is a need to identify and develop antimicrobial compounds that demonstrate selective toxicity towards microorganisms, but are not toxic, or have minimal (i.e., tolerable) toxicity, to animal hosts (e.g., humans).

SUMMARY OF THE INVENTION

The present invention provides methods for simultaneously assessing microbial phosphoglucose isomerase, ketol-isomerase and glucosamine-6-phosphate acetyltransferase activities, by measuring the production of Coenzyme A (CoA). The present invention finds use in the isolation of new classes of antifungal drugs, wherein the compounds have the ability to inhibit fungal glucose utilization.

In one embodiment, the present invention provides methods for the detection of phosphoglucose isomerase, ketol-isomerase and acetyltransferase activities in a sample, comprising the steps of a) providing: a sample suspected to contain phosphoglucose isomerase, ketol-isomerase and acetyltransferase activities, glucose-6-phosphate, glutamine, acetyl coenzyme A, and 5,5'-dithiobis(2-nitrobenzoic acid); b) combining the sample, glucose-6-phosphate, glutamine, and acetyl coenzyme A under conditions to yield reaction products comprising coenzyme A and N-acetylglucosamine-6-phosphate; c) inactivating the phosphoglucose isomerase, ketol-isomerase and acetyltransferase activities; and d) combining the reaction product comprising coenzyme A and 5,5'-dithiobis(2-nitrobenzoic acid) under conditions to yield a chromogenic reaction product comprising 2-nitro-thiobezoate anion, wherein the chromogenic reaction product is indicative of phosphoglucose isomerase, ketol-isomerase and acetyltransferase activities. In a related embodiment, the sample comprises a lysate selected from the group consisting of crude cell lysates and gel filtered cell lysates. In some embodiments, the lysate is a fungal cell lysate selected from the group consisting of Aspergillus cell lysates, Candida cell lysates, Cryptococcus cell lysates, Histoplasma cell lysates, Pneumocystis cell lysates, Rhizopus cell lysates, Saccharomyces cell lysates, and Schizosaccharomyces cell lysates. In one embodiment, the sample comprises purified fungal enzymes while in another embodiment the sample comprises recombinant fungal enzymes, where the fungal enzymes are selected from the group consisting of phosphoglucose isomerases, ketol-isomerases and acetyltransferases.

In other embodiments, the present invention provides methods for the detection of a compound having the ability to inhibit phosphoglucose isomerase, ketol-isomerase and/or acetyltransferase activities in a sample, comprising the steps of: a) providing a sample suspected to contain phosphoglucose isomerase, ketol-isomerase and acetyltransferase activities, glucose-6-phosphate, glutamine, acetyl coenzyme A, 5,5'-dithiobis(2-nitrobenzoic acid), and a candidate compound; b) preparing a first and second reaction mixture, where the first reaction mixture comprises the sample, glucose-6-phosphate, glutamine, and acetyl coenzyme A, and where the second reaction mixture comprises the sample, glucose-6-phosphate, glutamine, acetyl coenzyme A and the candidate compound; c) incubating the first and second reaction mixtures under conditions to yield reaction products comprising coenzyme A and N-acetylglucosamine-6-phosphate; d) inactivating the phosphoglucose isomerase, ketol-isomerase and acetyltransferase activities; e) combining the first and second reaction mixtures with 5,5'-dithiobis (2-nitrobenzoic acid) under conditions to yield a chromogenic reaction product comprising 2-nitro-thiobezoate anion; and f) comparing the quantity of the chromogenic reaction product in the first and second reaction mixtures. In a related embodiment, these methods further comprise step g) scoring the candidate compounds as positive for the ability to inhibit phosphoglucose isomerase, ketol-isomerase and/or acetyltransferase activities in a sample, when the second reaction mixture yields less than 50% of the chromogenic reaction product of the first reaction mixture. In other embodiments, the sample comprises a lysate selected from the group consisting of crude cell lysates and gel filtered cell lysates. In some embodiments, the lysate is a fungal cell lysate selected from the group consisting of Aspergillus cell lysates, Candida cell lysates, Cryptococcus cell lysates, Histoplasma cell lysates, Pneumocystis cell lysates, Rhizopus cell lysates, Saccharomyces cell lysates, and Schizosaccharomyces cell lysates. In one embodiment, the sample comprises purified fungal enzymes, while in another embodiment the sample comprises recombinant fungal enzymes, where the fungal enzymes are selected from the group consisting of phosphoglucose isomerases, ketol-isomerases and acetyltransferases. In some embodiments, the candidate compound is present in an extract selected from the group consisting of extremophile extracts, marine macroorganism extracts, cyanobacterial extracts and algal extracts.

In some embodiments, the present invention also provides compositions comprising at least one candidate compound which has the ability to inhibit phosphoglucose isomerase, ketol-isomerase and/or acetyltransferase activities in a sample, identified by methods comprising the steps of: a) providing a sample suspected to contain phosphoglucose isomerase, ketol-isomerase and acetyltransferase activities, glucose-6-phosphate, glutamine, acetyl coenzyme A, 5,5'-dithiobis(2-nitrobenzoic acid), and a candidate compound; b) preparing a first and second reaction mixture, where the first reaction mixture comprises the sample, glucose-6-phosphate, glutamine, and acetyl coenzyme A, and where the second reaction mixture comprises the sample, glucose-6-phosphate, glutamine, acetyl coenzyme A and the candidate compound; c) incubating the first and second reaction mixtures under conditions to yield reaction products comprising coenzyme A and N-acetylglucosamine-6-phosphate; d) inactivating the phosphoglucose isomerase, ketol-isomerase and acetyltransferase activities; e) combining the first and second reaction mixtures with 5,5'-dithiobis(2-nitrobenzoic acid) under conditions to yield a chromogenic reaction product comprising 2-nitro-thiobezoate anion; and f) comparing the quantity of the chromogenic reaction product in the first and second reaction mixtures. In a related embodiment, these compositions comprising at least one candidate compound which has the ability to inhibit phosphoglucose isomerase, ketol-isomerase and/or acetyltransferase activities in a sample are identified by methods which further comprise step g) scoring the candidate compounds as positive for the ability to inhibit phosphoglucose isomerase, ketol-isomerase and/or acetyltransferase activities in a sample, when the second reaction mixture yields less than 50% of the chromogenic reaction product of the first reaction mixture. In some embodiments, the candidate compound is present in an extract selected from the group consisting of extremophile extracts, marine macroorganism extracts, cyanobacterial extracts and algal extracts. In other embodiments, the candidate compound is present in a high performance liquid chromatography (HPLC) fraction of a microbial extract. In one embodiment, the candidate compound further has antifungal activity. In some embodiments, the antifungal activity is determined by a test selected from the group consisting of agar diffusion assays, broth dilution assays, and animal model assays. In preferred embodiments, the antifungal activity is selected from the group consisting of anti-Aspergillus activity, anti-Candida activity, anti-Cryptococcus activity, anti-Histoplasma activity, anti-Pneumocystis activity, anti-Rhizopus activity, anti-Saccharomyces activity, and anti-Schizosaccharomyces activity. In some embodiments the candidate compound further has limited toxicity to mammalian cells. In preferred embodiments, the mammalian cells are selected from the group consisting of murine cells and human cells. In a further preferred embodiment, the limited toxicity is determined by a test selected from the group consisting of in vitro and in vivo acute toxicity tests.

DEFINITIONS

Figure 1:
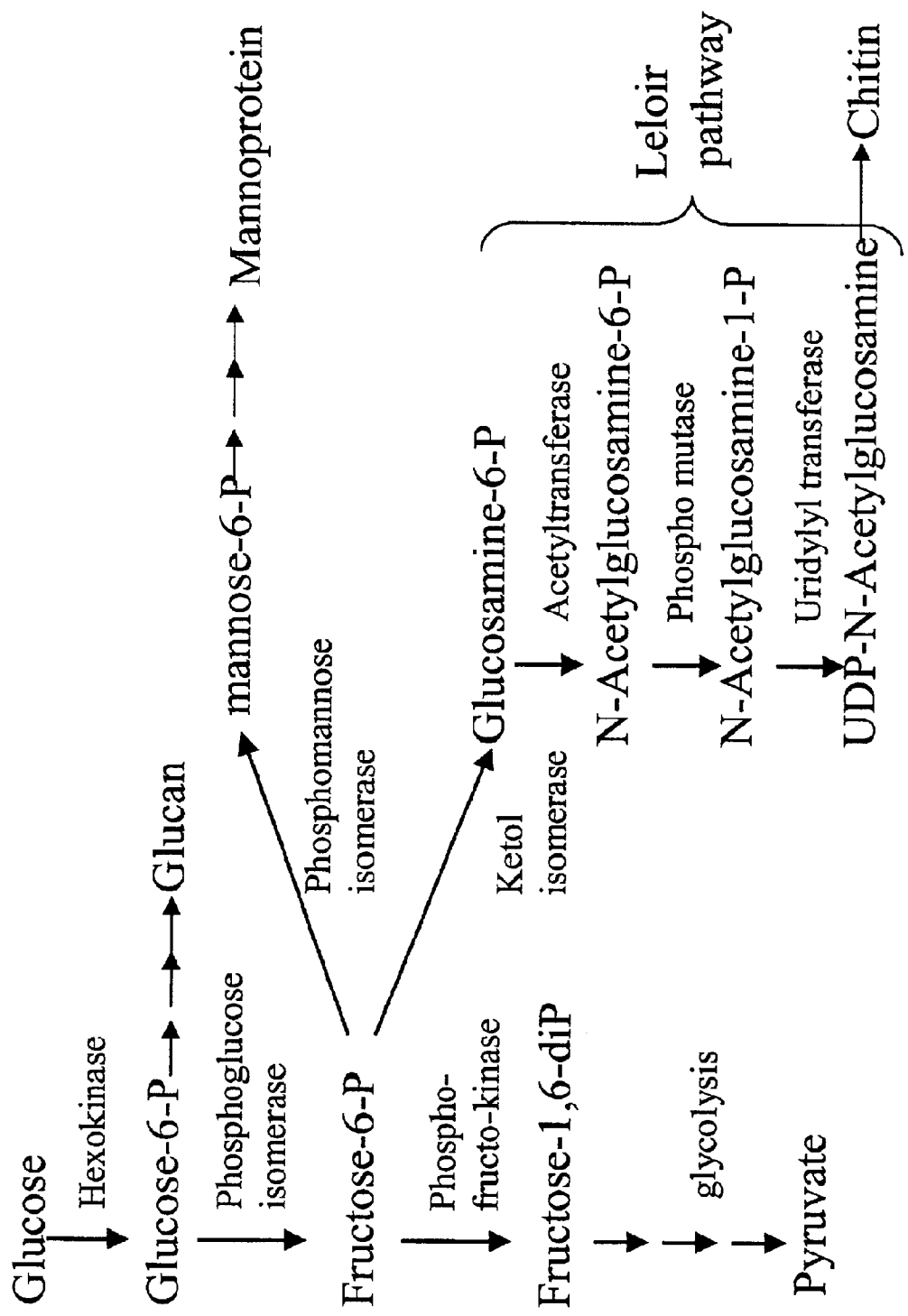
FIG. 1 shows the glucose metabolism pathways. Glucose is converted to pyruvate by glycolysis and also serves as a substrate for the production of cell-wall chitin and mannoproteins.

To facilitate understanding of the invention, a number of terms are defined and discussed below.

As used herein, the term "prokaryote" refers to organisms distinguishable from "eukaryotes." It is intended that the term prokaryote encompass organisms that exhibit the characteristics indicative of prokaryotes, such as possessing a single, circular chromosome, the lack of a true nucleus, the lack of membrane-bound organelles, and other molecular characteristics indicative of prokaryotes.

As used herein, the term "eukaryote" refers to organisms distinguishable from "prokaryotes." It is intended that the term eukaryote encompass all organisms with cells that exhibit the usual characteristics of eukaryotes such as the presence of a true nucleus bounded by a nuclear membrane within which reside the chromosomes, the presence of membrane-bound organelles, and other characteristics commonly observed in eukaryotic organisms. Thus, the term eukaryotes includes, but is not limited to, such organisms as fungi (e.g., molds, sac fungi, club fungi, yeasts), multicellular photosynthetic plants (e.g., corn, wheat, barley, soybean, potato, lettuce, rice, tobacco and alfalfa), protozoa (e.g., Acanthamoeba spp., Trypanosoma spp., Leishmania spp., Plasmodium spp., Toxoplasma spp., Giardia spp.), and animals (e.g., humans, cattle, sheep, goats, pigs, chickens, turkeys, dogs, cats, horses, reptiles).

The term "extremophile" as used herein refers to organisms which thrive in an extreme environment. Extreme environments include physical (i.e., temperature, radiation, pressure, etc.), geochemical (i.e., dessication, salinity, etc.), and biological (i.e., nutritional or population extremes, etc.) extremes. Extremophiles include but are not limited to thermophiles, xerophiles, halophiles, and anaerobes.

As used herein, the term "macroorganism" refers to organisms visible to the naked eye. "Marine macroorganisms" refer to organisms from the sea. In particular, the "marine macroorganisms" of the present invention include but are not limited to sponges, tunicates, slugs, corals, and sea fans. In contrast, the term "microorganism" refers to an organism that is too small to be visible without the aid of a microscope. "Microorganisms" include algae, bacteria, fungi, protozoa, and viruses.

The terms "cyanobacteria" and "cyanobacterial" refer to a genus of bacteria belonging to the class Oxyphotobacteria, which are composed of the blue-green algae. These organisms are also classified as algae in the division Cyanophyta.

As used herein, the terms "algae" and "algal" refer to mostly aquatic organisms that contain chlorophyll and other pigments and can carry on photosynthesis, but lack true roots, stems, or leaves. The term "algae" encompasses microscopic single cells to very large multicellular structures (e.g., seaweed).

The term "sample" as used herein is used in its broadest sense, and can refer to a sample of biological or non-biological origin. A sample of biological origin refers to any type of material obtained from animals or plants (e.g., any fluid or tissue), cultured cells or tissues, cultures of microorganisms (prokaryotic or eukaryotic), and any fraction or products produced from a living (or once living) culture. A sample may be a cell extract (i.e., a crude lysate) or contain intact cells. The molecule or compound of interest in a sample can be purified or unpurified (i.e., crude). An "experimental sample" is a sample where the presence, concentration and/or activity of some molecule or compound of interest is unknown. A "control sample" is a sample where the presence, concentration and/or activity of some molecule or compound of interest is known. For example, control samples containing known concentrations of some molecule or compound of interest (e.g., glutamate), can be used to determine the concentration of glutamate in an experimental sample by using an indicator assay (e.g., the nitro BT assay) to construct a standard concentration curve. As used herein, a sample "suspected of containing" a component or biological/biochemical activity is a sample where the presence of the component or activity has not been demonstrated or proven.

As used herein, a "drug" can be any molecule or any composition, including proteins, peptides, nucleic acids, organic molecules, inorganic molecules, and/or combinations of molecules, biological or non-biological, which are capable of producing a physiological response. As used herein, a "drug" provides at least one beneficial response in the cure, mitigation, treatment or prevention of a disease, condition or disorder (e.g., to treat a microbial infection). A compound is considered a "drug candidate" if it is not yet known if that compound will provide at least one beneficial response in the cure, mitigation, treatment or prevention of a disease, disorder or condition.

As used herein, the term "in vitro" refers to an artificial environment and to processes or reactions that occur within an artificial environment. The term "in vivo" refers to the natural environment (e.g., within an animal or within a cell) and to processes or reactions that occur within a natural environment. The definition of an in vitro versus in vivo system is particular for the system under study. For example, as used herein, assays for determining antifungal activity using the agar diffusion method is an in vitro assay system. Conversely, the determination of antifungal activity using a whole mouse candidiasis/candidosis model is an in vivo assay system.

As used herein, the term "subject" refers to any animal or plant being examined, studied or treated. It is not intended that the present invention be limited to any particular type of subject. It is contemplated that multiple organisms will find use in the present invention as subjects. In some embodiments of the present invention, humans are the preferred subject, while in other embodiments nonhuman animals are the preferred subject, including but not limited to cattle, sheep, goats, pigs, chicken, turkeys, dogs, cats, horses and reptiles). In other embodiments, plants are the subjects for treatment (e.g., corn, wheat, barley, soybean, potato, lettuce, rice, tobacco and alfalfa).

As used herein, the terms "inhibit" and "suppress" refer to the act of diminishing, suppressing, alleviating, preventing, reducing or eliminating. For example, a compound which inhibits microbial growth may kill all microbial cells (i.e., bacteriocidal or fungicidal action), or prevent, arrest or slow further microbial growth (i.e., bacteriostatic or fungistatic action). These terms are also used to describe the effect of a compound on an enzymatic activity. Thus, the terms "inhibit" and "suppress" as they apply to the analysis of enzymatic activity encompasses a range of effects, from completely eliminating to partially reducing. These terms find use in both in vitro as well as in vivo systems.

As used herein, the terms "local" and "localized" and the like refer to confinement to a small area or a single tissue (e.g., a small area on the skin). The term "localized delivery" is delivery of an agent (e.g., an antimicrobial compound) to a small area or single tissue. Localized delivery of an antimicrobial agent to the skin is termed "topical" delivery. A microbial infection may be "localized," (i.e., the infection is confined to a relatively small area or a single tissue, such as the skin), or may be "systemic" (i.e., the infection involves multiple sites, tissues or organs in a subject, typically via the circulatory or lymphatic systems). Similarly, delivery of an antimicrobial agent can be topical (e.g., where delivery is to the surface of the skin), or systemic (e.g., where delivery is by the circulatory system via an intravenous or intraarterial injection, or by gastrointestinal absorption if taken by mouth).

As used herein, the term "systemic delivery" (in contrast to localized delivery) involves delivery of an agent (e.g., a drug) to multiple sites, tissues or organs in an organism, or to the entire organism via the circulatory system following an intravenous injection, or via gastrointestinal absorption of an orally administered agent.

As used herein, the terms "antimicrobial," "antimicrobial chemotherapeutic," "antimicrobial drug," "antimicrobial compound" and "antimicrobial activity," are used in reference to any compound, substance or agent that inhibits the growth of microorganisms, including eukaryotic microorganisms (e.g., fungi) and prokaryotes (e.g., bacteria). Thus, antimicrobial agents comprise both antifungal and antibacterial agents. It is intended that the term be used in its broadest sense, and includes, but is not limited to, compounds that exist naturally (e.g., antibiotics) or compounds that are produced by artificial means (e.g, by in vitro chemical synthesis). Antimicrobials can be used with or on a subject in the treatment of microbial disease, infection, colonization or other pathology. Antimicrobials include compounds that kill or eliminate microbial growth as well as compounds that merely suppress, slow or arrest microbial growth. Antimicrobial activity can take place in vitro, as well as in vivo.

As used herein, the term "fungicidal" refers to an agent that kills fungi. In contrast, the term "fungistatic" refer to agents which slow or arrest the growth of fungi, but do not kill the organism.

The terms "antifungal," "antifungal agent," "antifungal chemotherapeutic," and "antifungal drug," as used herein, refer to any compound, substance or agent used in the treatment of fungal condition, disease, infection or colonization. It includes fungicidal as well as fungistatic compounds which act on fungi in vitro, as well as in vivo. Examples of antifungal agents include amphotericin B, nystatin, fluconazole, itraconazole, naftifine, ketoconazole, 5-fluorocytosine and griseofulvin. The antifungals of the present invention are not limited to any particular mechanism of action. Nor is an understanding of the mechanism of action necessary to use the antifungals of the present invention.

Examples of fungal conditions, diseases and infections include but are not limited to: adiaspiromycosis, aspergillosis, dermatophytoses, blastomycosis, candidemia, cercosporamycosis, systemic and superficial candidiasis (i.e., candidosis), chromoblastomycosis, chromomycosis, coccidioidomycosis, cryptococcosis, cryptomycosis, dermatomycosis, entomophthoramycosis, favus (tinea favosa), fusariosis, geotrichosis, histoplasmosis, hyalohyphomycosis, lobomycosis, maduramycosis (Madura foot), mycetoma, mucormycosis, mycotic keratitis, mycotic keratosis, onychomycosis, oomycosis, otomycosis, paracoccidiomycosis, penicillosis, phaeohyphomycosis, phaeomycotic cyst, piedras (black piedra, white piedra), pityriasis nigra, pityriasis versicolor (i.e., tinea versicolor), pneumonia, protothecosis, rhinosporidiosis, ringworm, sporotrichosis, systemic mycoses, tinea, torulopsosis, trichomycosis axillaris, and zygomycosis. These examples are intended to be exemplary only, and it is not intended that the present invention be limited in scope by these examples.

As used herein, the term "antimetabolite" refers to any substance with a close structural resemblance to another essential substance (i.e., a metabolite) that is required for normal physiologic function. Typically, antimetabolites exert growth inhibitory effects by interfering with the utilization of the metabolite. For example, 5-fluorocytosine is an antimetabolite with antifungal activity, and sulfanilamide and isoniazid are antimetabolite antibacterials.

As used herein, the term "toxicity" generally refers to deleterious, impairing or injurious effects caused by a compound on a cell or organism. Toxicity can display a range of severity from mild to severe. In the extreme, severe toxicity causes the death of a cell or organism, where mild toxicity may result in symptoms in an organism that do not significantly impact the fitness or well-being of the organism. As used herein, the term "limited toxicity" refers to mild forms of toxicity.

As used herein, "selective toxicity" refers to the phenomenon where a compound may have toxic effects in one organism or cell type, but does not have those effects on a second organism or cell type, or has fewer or milder toxic effects on a second organism or cell type compared to the first organism or cell type. For example, most preferred antimicrobial compounds are effective in treating infections in a subject because of the selective toxicity displayed by the antimicrobial compound, where the antimicrobial compound demonstrates severe toxicity towards the microorganism responsible for an infection in a host, but that compound does not show toxicity towards the subject being treated for the infection (e.g., a human). Selective toxicity may be relative (i.e., not absolute). For example, a compound that demonstrates potent antimicrobial activity may also have mild toxic effects (i.e., tolerable, manageable or minimal effects) on the host subject (e.g., a human) being treated. If the mild toxicity experienced by the subject does not significantly impact the fitness or long-term well-being of the subject, such toxicity may be acceptable in the treatment of the infection.

The term "phosphoglucose isomerase activity," as used herein, refers to that enzymatic activity catalyzed by the phosphoglucose isomerase enzyme. Phosphoglucose isomerase activity is that activity which catalyzes the formation of fructose-6-phosphate (Fru-6-P) from glucose-6-phosphate (Glu-6-P). The presence of phosphoglucose isomerase activity in a sample is indicative of the presence of the phosphoglucose isomerase enzyme in that sample. However, the absence of phosphoglucose isomerase activity in a sample does not necessarily imply the absence of the phosphoglucose isomerase enzyme, as the presence of an inhibitor may suppress the phosphoglucose isomerase activity, although the enzyme is present. As used herein, the addition, identification or detection of phosphoglucose isomerase activity implies the presence of the phosphoglucose isomerase enzyme.

As used herein, the term "ketol-isomerase activity" refers to that enzymatic activity catalyzed by the ketol-isomerase enzyme. Ketol-isomerase activity is that activity which catalyzes the formation of glucosamine-6-phosphate (GlcN-6-P) and glutamate (Glu) from fructose-6-phosphate (Fru-6-P) and glutamine (Gln). The presence of ketol-isomerase activity in a sample is indicative of the presence of the ketol-isomerase enzyme in that sample. However, the absence of ketol-isomerase activity in a sample does not necessarily imply the absence of the ketol-isomerase enzyme, as the presence of an inhibitor may suppress the ketol-isomerase activity, although the enzyme is present. As used herein, the addition, identification or detection of ketol-isomerase activity implies the presence of the ketol-isomerase enzyme.

The term "acetyl transferase activity," as used herein, refers to that enzymatic activity catalyzed by the acetyl transferase enzyme. Acetyl transferase activity is that activity which catalyzes the formation of N-acetylglucosamine-6-phosphate (GlcNAc-6-P) and Coenzyme A (CoA) from glucosamine-6-phosphate (GlcN-6-P) and acetyl-Coenzyme A (AcCoA). The presence of acetyl transferase activity in a sample is indicative of the presence of the acetyl transferase enzyme in that sample. However, the absence of acetyl transferase activity in a sample does not necessarily imply the absence of the acetyl transferase enzyme, as the presence of an inhibitor may suppress the acetyl transferase activity, although the enzyme is present. As used herein, the addition, identification or detection of acetyl transferase activity implies the presence of the acetyl transferase enzyme.

DESCRIPTION OF THE INVENTION

The present invention provides methods for simultaneously assessing microbial phosphoglucose isomerase, ketol-isomerase and glucosamine-6-phosphate acetyltransferase activities, by measuring the production of Coenzyme A (CoA). The present invention finds use in the isolation of new classes of antifungal drugs, wherein the compounds have the ability to inhibit fungal glucose utilization.

Glucose Metabolism Pathways

The generation of metabolic energy by glycolysis is a nearly universal pathway in biological systems. In mammals, absorbed glucose is carried by the blood and is utilized by the tissues. Other sugars, such as fructose and galactose, are changed into glucose in the liver and used in the tissues. Under aerobic conditions, glucose is utilized via the citric acid cycle in the cytosol and the respiratory chain in mitochondria. Yeast (*Saccharomyces cerevisiae*) can utilize glucose under both aerobic and anaerobic conditions.

Glucose enters the glycolysis pathway by phosphorylation to glucose-6-phosphate (Glc-6-P), formed by the enzyme hexokinase. In the second step of the glycolysis pathway, phosphoglucose isomerase (EC 5.3.1.9) converts Glc-6-P to fructose-6-phosphate (Fru-6-P). After several sequential reactions, the final product, pyruvate, is formed (FIG. 1). In addition, Fru-6-P serves as the substrate for pathways leading to formation of cell-wall chitin and mannoproteins (FIG. 1).

The most striking difference between fungal cells and human cells is that fungal cells are encased in a wall that protects them from an osmotically and immunologically hostile external environment. In fungi, glucose is a key compound not only as an energy source, but also as a precursor of cell-wall synthesis. As shown in Table 1, yeast cell walls consist of roughly equimolar amounts of fibrous (1,3)β-glucan, (1,6)β-glucan, mannoprotein, and submolar amounts of chitin (Lipke et al., *J. Bacteriol.* 185:3735–3740 [1998]; and Smits et al., *Curr. Opin. Microbiol.* 2:348–352 [1999]). Chitin, although a minor component of yeast and filamentous fungal cell walls, is essential for cell viability and mother-daughter cell separation (McCullough, *New Approaches for Antifungal Drugs* [1992]; and Mio et al., *J. Bacteriol.* 178:2416–2419 [1996]).

TABLE 1

Major Components of *S. cerevisiae* Cell Walls

| component (degree of polymerization) | mean MW (kDa) | % of wall mass | relative molar ratio |
|---|---|---|---|
| (1,3)β-glucan (1500) | 240 | 50 | 1.0 |
| (1,6)β-glucan (150) | 24 | 10 | 2 |
| mannoprotein | 100–200 | 40 | 1.2–2.4 |
| chitin (120) | 25 | 1–3 | 0.1–0.3 |

Chitin Precursor Synthesis: The Leloir Pathway

Figure 2:
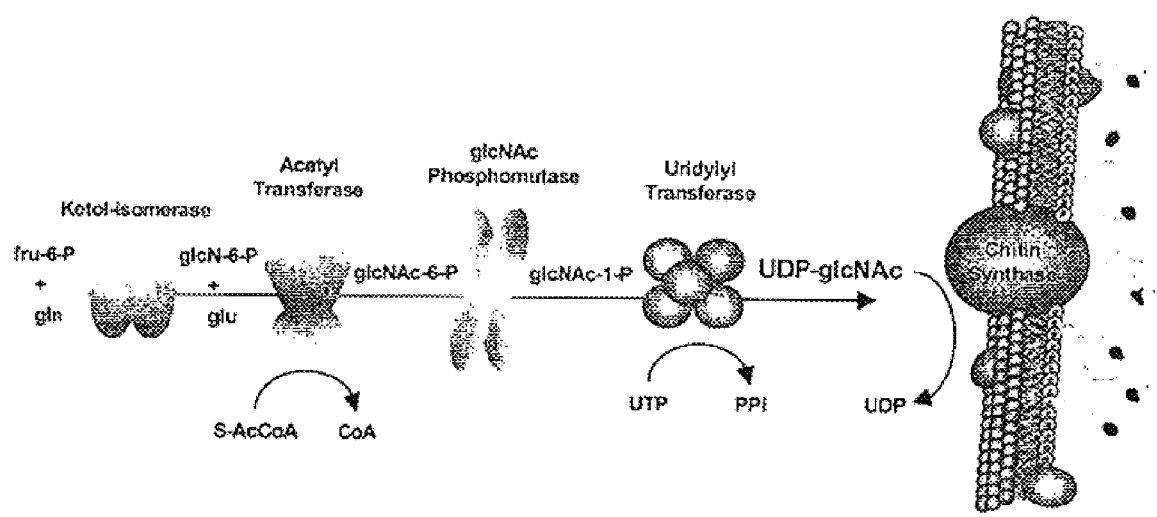
FIG. 2 shows the Leloir enzymatic pathway. Through the reactions of this pathway, the chitin precursor UDP-N-acetylglucosamine (UDP-GlcNAc) is produced from fructose-6-phosphate and glutamine. The chitin synthase step is also indicated, although this step is not formally part of the Leloir pathway.

The pathway for chitin precursor synthesis, known as the Leloir pathway, is shown in FIG. 2.

The first pathway specific enzyme is 2-deoxy-D-glucose-6-phosphate ketol-isomerase (EC 2.6.1.16). This enzyme forms glucosamine-6-phosphate (GlcN-6-P) and glutamate (Glu) from Fru-6-P and glutamine (Gln) (Selitrennikoff and Sonneborn, *Develop. Biol.* 54:37–51 [1976]).

The second enzyme in the pathway is aminodeoxyglucosephosphate N-acetyltransferase (EC 2.4.1.4). This enzyme converts acetyl CoA (AcCoA) and GlcN-6-P to CoA and N-acetylglucosamine-6-phosphate (GlcNAc-6-P) (Selitrennikoff and Sonneborn, *Develop. Biol.* 54:37–51 [1976]).

The third enzyme is acetylaminodeoxyglucose phosphomutase (EC 2.7.5.2), which converts GlcNAc-6-P to GlcNAc-1-P with glucose-1,6-di-phosphate as a cofactor (Selitrennikoff and Sonneborn, *Develop. Biol.* 54:37–51 [1976]).

The last enzyme is UTP:acetylaminodeoxyglucose-1-phosphate uridylyl transferase (EC 2.7.7.23) which converts GlcNAc-1-P and UTP to UDP-GlcNAc and PPi (Selitrennikoff and Sonneborn, *Develop. Biol.* 54:37–51 [1976]).

Finally, chitin synthase (EC 2.4.1.16) forms chitin, a (1,4)β-linked polymer of GlcNAc, from UDP-GlcNAc.

Phosphoglucose Isomerase

Phosphoglucose isomerase (EC 5.3.1.9) is an aldose-ketose isomerase, which catalyzes the interconversion of Glc-6-P and Fru-6-P, and plays a central role in the metabolism of phosphorylated sugars. The amino acid sequences of phosphoglucose isomerases are similar among fungi (yeast, *Neurospora crassa* and *Rhizopus oryzae*), parasites, and humans; the percentages of homologies range between 54 and 58% (Nakata, unpublished; and Marchand et al., *Eur. J. Biochem.* 184:455–464 [1989]). Recently, crystal structure analysis (Sun et al., *Proc. Natl. Acad. Sci. USA* 96:5412–5417 [1999]) and mutational analysis (Meng et al., *Protein Sci.* 8:2438–2443 [1999]) revealed that several amino acids in the active site are well conserved in these species. In spite of the amino acid similarity between humans and *Trypanosoma brucei* (54%), the enzyme is being developed as a therapeutic target for treatment of *T. brucei* infections in humans (Hardre et al., *J. Enzyme Inhib.* 15:509–515 [2000]).

TABLE 2

Predicted Charge of Phosphoglucose Isomerase

| | Positive Charge | | | Negative Charge | | | |
|---|---|---|---|---|---|---|---|
| Organism | Lys | Arg | Total | Asp | Glu | Total | Net |
| *T. brucei* | 31 | 32 | 63 | 29 | 36 | 65 | −2 |
| Yeast | 40 | 10 | 50 | 25 | 35 | 60 | −10 |
| Mouse | 41 | 20 | 61 | 25 | 35 | 60 | +1 |
| Pig | 38 | 24 | 62 | 25 | 36 | 61 | +1 |
| Human | 35 | 27 | 62 | 27 | 32 | 59 | +3 |

Although the comparison of the amino acid sequences between yeast and the other phosphoglucose isomerases (e.g., mammals and *T. brucei*) shows 54–58% identity, the yeast enzyme shows some unique characteristics (Marchand et al., supra [1989]) as compared to the mammalian and *T. brucei* enzymes. In the first place, yeast and other fungal phosphoglucose isomerases have fewer positively charged amino acids. Accordingly, the net charge of fungal phosphoglucose isomerase is negative, while the others are almost neutral (Table 2), resulting in differences in their iso-electric points. Secondly, at higher ionic strength (more than 0.1 M), the $K_m$ for Fru-6-P of the yeast enzyme increased compared to the others, although there were no differences in $K_m$ among these species at low ionic strength. This likely reflects amino acid sequence differences at some distance from the active site. Thirdly, at low ionic strength, the $K_i$ of a competitive inhibitor, gluconate-6-phosphate, of the yeast phosphoglucose isomerase was at least 3 times higher than that of the others, whereas the $K_m$ for Fru-6-P was very similar for these enzymes (Table 3). Lastly, as shown in Table 4, D-arabinonhydroxamic acid-5-phosphate displays a 4.6-fold specificity for *T. brucei* phosphoglucose isomerase versus yeast isomerase (Hardre et al., supra [2000]). This is likely the result of the presence of more positively charged residues in the active site of *T. brucei* phosphoglucose isomerase as compared to yeast enzyme. Thus, significant differences between fungal and other phosphoglucose isomerases exist, which can be exploited for the isolation of specific fungal inhibitors.

TABLE 3

Kinetic Constants of Phosphoglucose Isomerase (mM)

| Organism | Fru-6-P $K_m$ | Gluconate-6-P $K_i$ |
|---|---|---|
| T. brucei | 0.122 ± 0.045 | 0.14 ± 0.03 |
| Yeast | 0.167 ± 0.048 | 0.48 ± 0.12 |
| Rabbit | 0.119 ± 0.028 | 0.12 ± 0.03 |

TABLE 4

Inhibition Property of D-Arabinohydroxamic acid-5-phosphate

| T. brucei PGI | | Yeast PGI | | |
|---|---|---|---|---|
| $K_i$ ($\mu$M) | $K_m/K_i$ | $K_i$ ($\mu$M) | $K_m/K_i$ | $K_i^T/K_i^Y$ |
| 0.050 ± 0.009 | 2060 | 0.23 ± 0.02 | 300 | 4.6 |

Phosphoglucose isomerase deficient mutants of *S. cerevisiae* have been isolated (Clifton et al., *Genetics* 88:1–11; Herrera and Pascal, *J. Gen. Microbiol.* 108:305–310 [1978]; and Navon et al., *Biochemistry* 18:4487–4499 [1979]). These mutants do not grow on/in glucose-containing media. Although the mutants are able to grow in rich medium containing 2% fructose, 2% glucose inhibits their growth (Navon, supra [1979]). Interestingly, mutants with low enzyme activity (about 1% of wild type) grew on fructose alone, while mutants with essentially no enzyme activity (less than 1% of wild type) grew on fructose only if provided with a small quantity of glucose. In addition, glucose concentrations higher than 0.4 mg/mL inhibited the growth of both mutants on fructose-containing media. Apparently the mutants need a large amount of fructose for glycolysis, pentose monophosphate pathways and cell wall synthesis, and that at least similar and larger quantities of glucose compared to fructose inhibit the growth of mutants due to the accumulation of Glc-6-P and its toxicity. Thus inhibitors of fungal phosphoglucose isomerase would have a deleterious effect on fungal glucose utilization. These results indicate that phosphoglucose isomerase is essential for fungal growth and accordingly is a useful target for antifungal drugs.

Ketol-Isomerase

The first enzyme in the Leloir pathway is 2-amino-2-deoxy-D-glucose-6-phosphate ketol-isomerase (ketol-isomerase), which is also referred to as glutamine: fructose-6-phosphate amidotransferase and glucosamine-6-phosphate synthase. The enzyme has been found in mammals including humans (McKnight et al., *J. Biol. Chem.* 267:25208–25212 [1992]; and Winterburn and Phelps, *Biochem. J.* 121:701–709 [1971]), fungi (Etchebehere and Maia, *Arch. Biochem. Biophys.* 272:301–310 [1989]; Endo et al., *J. Bacteriol.* 103:588–594 [1970]; Smith et al., *J. Bacteriol.* 178:2320–2327 [1996]; Watzele and Tanner, *J. Biol. Chem.* 264:8753–8758 [1989]; and Borgia, *J. Bacteriol.* 174:384–389 [1992]), and bacteria (Badet et al., *Biochemistry* 26:1940–1948 [1987]; and Zhou et al., *Diabetes* 47:1836–1840 [1998]). Ketol-isomerase forms GlcN-6-P and glutamate from Fru-6-P and glutamine. The product, GlcN-6-P, is a precursor of UDP-N-acetylglucosamine (UDP-GlcNAc), which is the major intermediate of numerous macromolecules containing glycoproteins, proteoglycans, and glycolipids in mammals, chitin and mannoproteins in fungi, peptidoglycan and lipopolysaccharides in bacteria.

Eukaryotic ketol-isomerases are feedback-inhibited by UDP-GlcNAc, which is the end product of the Leloir pathway. One important distinction between fungal and mammalian ketol-isomerases is that the sensitivity of the fungal enzyme to UDP-GlcNAc is dependent on the phosphorylation state of the ketol-isomerase (i.e., the enzyme is only feedback-inhibited when phosphorylated). In contrast, phosphorylation does not play a role in mammalian ketol-isomerase regulation (McKnight et al., supra [1992]; and Endo et al., supra [1970]).

The amino acid sequences of ketol-isomerases of yeast and *C. albicans* (GFA1) exhibit 54% and 35% identity to those of human (humanGFAT) and *Escherichia coli* (glmS), respectively. While there are regions of conserved amino acids sequence, there are regions of significant sequence divergence between human, fungal, and bacterial ketol-isomerases (Nakata, unpublished BLAST analysis). For example, human ketol-isomerase has two phosphorylation sites in the hinge region between the glutamine- and Fru-6-P-binding domains; on the other hand, yeast has only one phosphorylation site, and *E. coli* has none (Zhou et al., supra [1998]).

Mutations that reduce ketol-isomerase activity result in the inhibition of fungal growth due to a reduced amount of chitin in cell walls, leading to osmotic sensitivity and fungal cell lysis (Katz and Rosenberger, *Biochim. Biophys. Acta.* 208:452–460; and Russell and Srb, *Mol. Gen. Genet.* 129:77–86 [1974]). Importantly, compounds that inhibit fungal ketol-isomerase activity also inhibit *C. albicans* growth (Milewski et al., *Antimicrob. Agents Chemother.* 35:36–43 [1991]). Ketol-isomerase has not been previously exploited as a target for antifungal agents (Milewski et al., supra [1991]; and Selitrennikoff and Ostroff, *Emerging Therapeutic Targets* 3:53–72 [1999]).

N-Acetyltransferase

The second enzyme in the Leloir pathway is aminodeoxyglucosephosphate N-acetyltransferase (acetyltransferase), which is also called glucosamine-6-phosphate N-acetyltransferase. Glucosamine-6-phosphate N-acetyltransferase encoding genes have been identified in *S. cerevisiae* (ScGNA1) (Mio et al., *J. Biol. Chem.* 274:424–429 [1999]), *C. albicans* (CaGNA1) (Mio et al., supra [1999]), and mice (Emeg32)(Boehmelt et al., *J. Biol. Chem.* 275:12821–12832 [2000]). In humans, the glucosamine-6-phosphate N-acetyltransferase gene has not been reported. A search of databases for human N-acetyltransferases revealed the existence of three closely related N-acetyltransferases (spermidine/spermine N-acetyltransferase [GenBank™ accession number U40369]; arylamine N-acetyltransferase [GenBank™ accession number X14672]; and putative N-acetyltransferase mRNA [GenBank™ accession number AF185571]). The comparison of the amino acid sequences of N-acetyltransferase signature motifs is shown in Table 5 (Mio et al., supra [1999]; and Boehmelt et al., supra [2000]). The sequences in the signature motifs are somewhat conserved in all species. In contrast, the entire amino acid sequence of CaGNA1 shows 35% identity to that of Emeg32, and no significant similarity to human N-acetyltransferases.

TABLE 5

Comparison of N-Acetyltransferase Motifs

| Gene[1] | Domain I[2]<br>UEDUUUXXXURGXGUG$XUU<br>(SEQ ID NO:1) | Domain II<br>NXPAUXUYX+UGJ<br>(SEQ ID NO:2) | CaGNA1<br>%<br>Identity |
|---|---|---|---|
| CaGNA1 | IEDISVAKSEQGKKLGYYLV<br>(SEQ ID NO:3) | N---VGFYEKCGY<br>(SEQ ID NO:4) | 100% |
| ScGNA1 | IEDIAVNSKYQGQGLGKLLI<br>(SEQ ID NO:5) | N---VKFYEKCGF<br>(SEQ ID NO:6) | 43% |
| Emeg32 | VEDVVVSDECRGKQLGKLLL<br>(SEQ ID NO:7) | N---VGFYKKFDY<br>(SEQ ID NO:8) | 35% |
| SSAT | LEDFFVMSDYRGFGIGSEIL<br>(SEQ ID NO:9) | NEPSINFYKRRGA<br>(SEQ ID NO:10) | -[3] |
| AA-NAT | YSTGMVHLLLQVTIDGRNYI<br>(SEQ ID NO:11) | IE---AYFERIGY<br>(SEQ ID NO:12) | - |
| ?-NAT | LFHLSVDNEHRGQGIAKALV<br>(SEQ ID NO:13) | QLSAMGLYQSLGF<br>(SEQ ID NO:14) | - |

[1]CaGNA1/*C. albicans* GlcN-6-P acetyltransferase;
ScGNA1/*S. cerevisiae* GlcN-6-P acetyltransferase;
Emeg32/murine GlcN-6-P acetyltransferase; SSAT/
human spermidine/spermine N1-acetyltransferase;
AA-NAT/human arylamine N-acetyltransferase; and
?-NAT/human putativeN-acetyltransferase.
[2]Consensus abbreviations: $ = Ser or Thr; J = Tyr
or Phe; U = bulky hydrophobic; + = positively
charged; and X = any amino acid.
[3]No significant identity.

In *S. cerevisiae*, the deletion of GNA1 is lethal as GNA1-deficient mutants swell and lyse (Mio et al., supra [1999]). Although *C. albicans* GNA1 deficient mutants cannot grow on glucose-containing medium, the mutants can grow in the presence of 2% GlcNAc (Mio et al., *Microbiology* 146:1753–1758 [2000]). This is because the aminohexose transport system of *C. albicans* is different from that of *S. cerevisiae*. *C. albicans* has GlcNAc permease, but *S. cerevisiae* does not. In *C. albicans*, GlcNAc is transported into the cells by GlcNAc permease, and then converted to GlcNAc-6-P by N-acetylglucosamine kinase, and GlcNAc-6-P is metabolized into Fru-6-P (Mio et al, supra [2000]; Singh and Datta, *Biochem. J.* 178:427–431 [1979]; Gopal et al., *J. Gen. Microbiol.* 128:2319–2326 [1982]; and Datta et al., *Adv. Microb. Physiol.* 30:53–88). Although GNA1-deficient mutants of *C. albicans* can grow in vitro in the presence of GlcNAc, the virulence of the mutants was significantly attenuated in a mouse infection model (Mio et al., supra [2000]). It seems that GNA1 is an essential gene for virulence because the amount of GlcNAc in host tissues and blood is insufficient for the in vivo growth of *C. albicans*. In summary, each of these three enzymes is essential for fungal growth and/or virulence. In addition, there exists significant differences between each of the fungal and mammalian enzymes, and lastly, each enzyme has heretofore been an unexploited target for antifungal drugs.

Previous in vitro Assays for Phosphoglucose Isomerase

Generally, phosphoglucose isomerase activity has been assayed in vitro spectrophotometrically using a coupled enzymatic reaction with glucose-6-phosphate dehydrogenase (Noltmann, *Methods Enzymol.* 9:557–565 [1966]). Enzyme activity is determined by monitoring the rate of NADH formation as measured by absorbance increase at 340 nm. This method has the disadvantage of identifying glucose-6-phosphate dehydrogenase inhibitors, as well as phosphoglucose isomerase inhibitors.

Previous in vitro Assays for Ketol-Isomerase

The Morgan-Elson assay (Zalkin, *Methods Enzymol.* 113:278–281 [1985]) is often used to determine the amount of one product, GlcN-6-P, formed by ketol-isomerase activity. This method requires boiling (twice), centrifugation, and the addition of an unstable compound, acetic anhydride to convert GlcN-6-P to GlcNAc-6-P. Therefore, this method is not suitable for low throughput screening, much less high throughput screening. On the other hand, the other product, glutamate, is measured using a coupled reaction with glutamate dehydrogenase (Badet et al., supra [1987]). The principle and the problems of this method to screen for inhibitors are similar to those of the glucose-6-phosphate dehydrogenase-coupled method (described above).

Previous in vitro Assays for N-Acetyltransferase

N-acetyltransferase converts AcCoA into CoA and forms GlcNAc-6-P from GlcN-6-P. Traditionally, the amount of GlcNAc-6-P formed has been determined using the Morgan-Elson assay. As indicated above, the Morgan-Elson assay is not suitable for either low or high throughput screening. On the other hand, CoA reacts with 5,5'-dithiobis(2-nitrobenzoic acid) (DTNB) and releases the 2-nitro-thiobezoate anion (TNB), which has a high molar absorption coefficient (Riddles et al., *Methods Enzymol.* 91:49–61 [1983]). This chemical reaction is fast and sensitive with few side reactions. Thus, the reaction finds use in high throughput screening.

Figure 3:
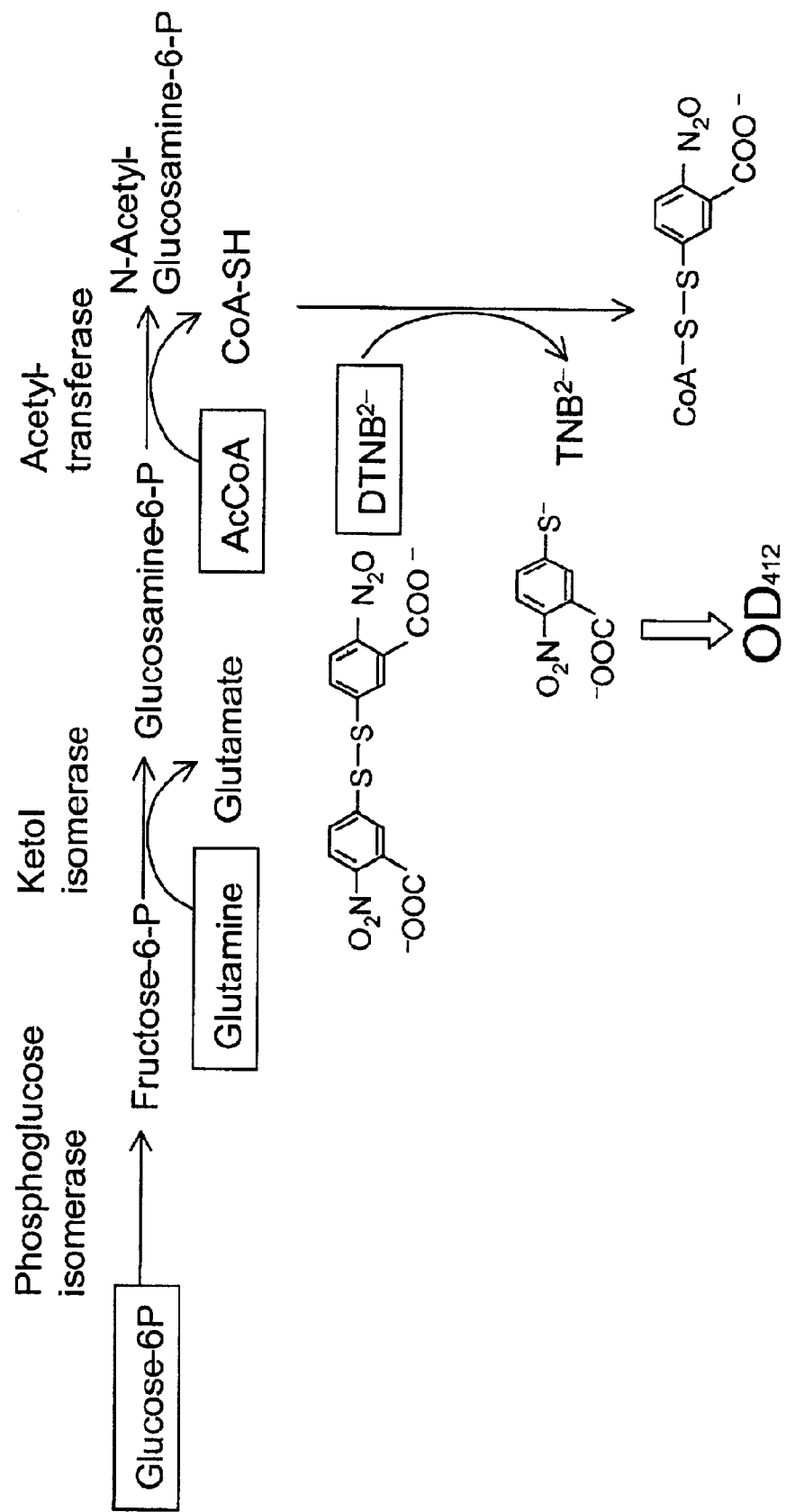
FIG. 3 shows a schematic of the reactions measured in the glucose utilization assay/CoA formation assay of the present invention. Phosphoglucose isomerase, ketol-isomerase and acetyltransferase activities are simultaneously monitored by measuring the production of CoA(GlcNAc-6-P) with a spectrophotometer. Boxed compounds are added into crude lysates in this assay.

New Method to Assay Phosphoglucose Isomerase, Ketol-Isomerase, and N-Acetyltransferase Activities As described herein, each of these three enzymes, phosphoglucose isomerase, ketol-isomerase and N-acetyltransferase, provides useful targets for antifungal drugs. As described above, the enzyme assay methods used previously, except for the DTNB assay, are not suitable for high throughput screening. In contrast, the present invention provides high throughput methods to simultaneously screen for inhibitors of these three enzymes. FIG. 3 provides a summary of the reactions involved in one embodiment of the assay system of the present invention. In a crude extract of a pathogenic fungus, prepared from mid-log growth phase cells, Glc-6-P is converted to Fru-6-P by phosphoglucose isomerase. The resulting Fru-6-P is then converted to GlcN-6-P by ketol-isomerase activity and finally to GlcNAc-6-P by the action of the N-acetyltransferase. In this method, only exogenous Glc-6-P, glutamine and AcCoA are needed as substrates. After termination of in vitro reactions by the addition of guanidine hydrochloride, DTNB is added. The amount of CoA produced (i.e., GlcNAc-6-P produced), is determined by measurement of the optical density (OD) at 412 nm.

In preferred embodiments of the assay of the present invention, no exogenous enzymes need to be added. Therefore, the risk of detecting false-positives is minimized. In addition, the present invention provides the means to simultaneously screen for inhibitors of each of these three enzymes. The methods of the present invention are fast, sensitive and inexpensive. Importantly, the present invention solves a long-felt need in the art for methods to identify new classes of compounds which have antifungal therapeutic activity.

In sum, the present invention provides improved methods for the simultaneous assay of fungal phosphoglucose isomerase, ketol-isomerase and glucosamine-6-phosphate acetyltransferase activities. In preferred embodiments, the present invention provides methods for photometrically measuring fungal Coenzyme A production, through the addition of 5,5'-dithiobis(2-nitrobenzoic acid). The present invention further provides methods for drug screening to identify compounds that have the ability to inhibit fungal glucose utilization. It is contemplated that compounds that inhibit fungal glucose metabolism will also have antifungal activity. Thus, it is contemplated that these compounds will find use in the treatment of fungal infections. An understanding of the mechanism(s) by which a compound inhibits fungal phosphoglucose isomerase, ketol-isomerase or glucosamine-6-phosphate acetyltransferase activity and/or imparts antifungal activity is not necessary in order to make or use the present invention. In addition, it is not intended that the present invention be limited to any particular mechanism(s) of inhibition of fungal glucose utilization or antifungal action.

Experimental

The following Examples are provided in order to demonstrate and further illustrate certain preferred embodiments and aspects of the present invention and are not to be construed as limiting the scope thereof.

As used herein, the following scientific abbreviations/notations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); mL (milliliters); $\mu$L (microliters); cm (centimeters); mm (millimeters); $\mu$m (micrometers); nm (nanometers); MW (molecular weight); °C. (degrees Centigrade); OD (optical density); EDTA (ethylenediamine-tetracetic acid); SDS (sodium dodecyl sulfate); PAGE; UV (ultraviolet); $\mu$g/mL (microgram per milliliter); mm (millimeter); ×g (times gravity); HPLC (high pressure liquid chromatography); DDT (dithiothreitol); DMSO (dimethyl sulfoxide); PMSF (phenylmethylsulfonyl fluoride); SDS (sodium dodecyl sulfate); s and sec (seconds), m and min (minutes), h and hr (hours), w/v (weight to volume measure), v/v (volume to volume measure).

As used herein, the following abbreviations apply: ATCC (American Type Culture Collection, Manassas, Va.); Beckman Instruments, Inc. (Beckman Instruments, Inc., Fullerton, Calif.); Charles River Laboratories (Charles River Laboratories, Inc., Wilmington, Mass.); Clonetech (Clonetech, Palo Alto Calif.); DIFCO or Difco (Difco Laboratories, Detroit, Mich.); Fisher (Fisher Scientific, Pittsburgh, Pa.); Gibco-BRL or BRL or Life Technologies (GIBCO BRL Life Technologies, Gaithersburg, Md.); ICN (ICN Biochemicals, Inc., Costa Mesa, Calif.); Molecular Devices (Molecular Devices Corp., Sunnyvale, Calif.); MycoLogics (MycoLogics Inc., Denver, Colo.); Promega (Promega Corp., Madison, Wis.); Sigma (Sigma Chemical Company/Aldrich, St. Louis, Mo.); Stratagene (Stratagene, La Jolla, Calif.); and Whatman (Whatman, Inc., Clifton, N.J.).

EXAMPLE 1

Preparation of *Aspergillus fumigatus* Crude Cell Lysates

In this Example, the growth, harvesting and preparation of *Aspergillus fumigatus* crude cell lysates are described. The resulting crude cell extract is used to measure the amount of CoA(GlcNAc-6-p) formed in the phosphoglucose isomerase, ketol isomerase and acetyltransferase reactions described in Example 2.

*A. fumigatus* ATCC16424 (a human clinical isolate) was inoculated into liquid YG medium [1% (w/v) yeast extract and 1% (w/v) glucose] with 1×10$^7$ conidia per/mL (final concentration), and incubated for 18 hours at 37° C. with shaking (250 rpm). Hyphae were harvested by vacuum filtration over Whatman No. 2 filter paper, washed twice with ice-cold water, quick-frozen in dry ice, and stored at −80° C.

Frozen *A. fumigatus* hyphae were thawed and disrupted by bead-beating (6×30 seconds pulses with 2 minutes cooling between each pulse) using 0.5 mm zirconium beads in KI buffer (600 mM sucrose, 1 mM KCl, 1 mM EDTA, 50 mM PIPES, pH 6.8). The lysates were centrifuged at 1,000×g for 10 minutes at 4° C. The supernatants were stored at −80° C. and used as enzyme sources. The protein concentration of the supernatants was determined using the BioRad protein assay kit.

EXAMPLE 2

Phosphoglucose Isomerase, Ketol-Isomerase, and N-Acetyltransferase Assays

In this Example, colorimetric methods used to measure fungal CoA formation are described. In particular, these methods were developed to quantitate CoA formation by the sequential action of *A. fumigatus* phosphoglucose isomerase, ketol-isomerase, and N-acetyltransferase.

Figure 4:
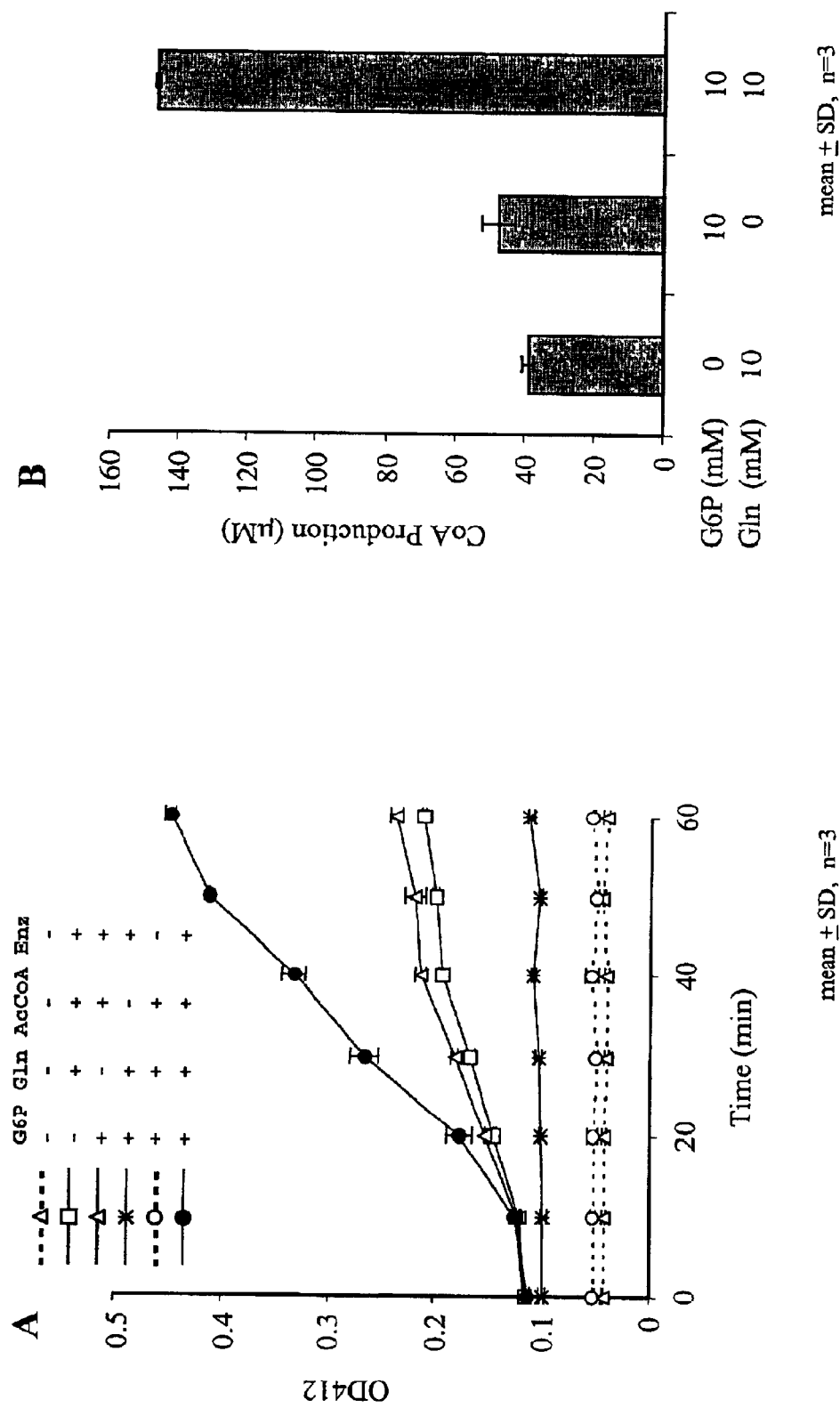
FIG. 4 shows the results obtained by using this method to measure fungal glucose utilization, by quantitating phosphoglucose isomerase, ketol-isomerase and acetyltransferase activities, after addition of the substrates glucose-6-phosphate, glutamine and acetyl-CoA, to crude A. fumigatus lysates. Panel A shows a time course of CoA production indicating that complete reactions were linear over the course of 10 to 50 minutes. Panel B shows the concentration of CoA after a 50 min incubation. Clearly, by omitting one substrate from the reaction, the sequential action of the three enzymes can be quantitated.

Reactions were performed in 96-well flat bottom microtiter plates containing 10 mM Glc-6-P, 10 mM glutamine, 200 $\mu$M AcCoA, and 0.25 mg/mL cell lysate of *A. fumigatus* at pH 6.8 in a final volume of 50 $\mu$L. Reactions were started by the addition of the cell lysate, incubated at 37° C. for various times, and stopped by the addition of 50 $\mu$L of 6.4 M guanidine hydrochloride. Subsequently, 50 $\mu$L of 200 mM DTNB was added. After incubation for 10 minutes at room temperature, the OD$_{412}$ was measured using a microtiter plate reader. CoA standards (in lysate) were also assayed in parallel, in order to generate a standard curve. The amount of CoA formed by reaction mixtures was calculated from the standard curve. Controls included mixtures lacking Glc-6-P, glutamine, AcCoA, crude enzyme, or all of them. The experiment was performed in triplicate. These results are shown in FIG. 4.

The formation of CoA by complete reactions was linear from 10 to 50 minutes (FIG. 4, a; closed circles) and exceeded that formed by control mixtures. At 50 minutes of incubation, 146 $\mu$M (7.3 nmol) of CoA was formed (12 nmol CoA formed/mg protein/min). In control mixtures lacking AcCoA or crude enzyme (dashed lines), the OD$_{412}$ did not increase during the incubation. However, in control mixtures lacking one substrate, Glc-6-P or glutamine, ~2.3 nmoles of CoA were formed at 50 minutes (solid lines, open symbols). These results show that although backgrounds are present (perhaps due to the presence of endogenous substrates present in crude lysates), CoA formation by the sequential action of the three enzymes can be easily quantitated using this simple assay.

EXAMPLE 3

Detection of Inhibitors of Gluconate-6-Phosphate and UDP-GlcNAc

In this Example, the use of the colorimetric CoA (GlcNAc-6-P) formation assay, to quantitate the effect of known inhibitors of phosphoglucose isomerase and gluconate-6-phosphate, is described.

Figure 5:
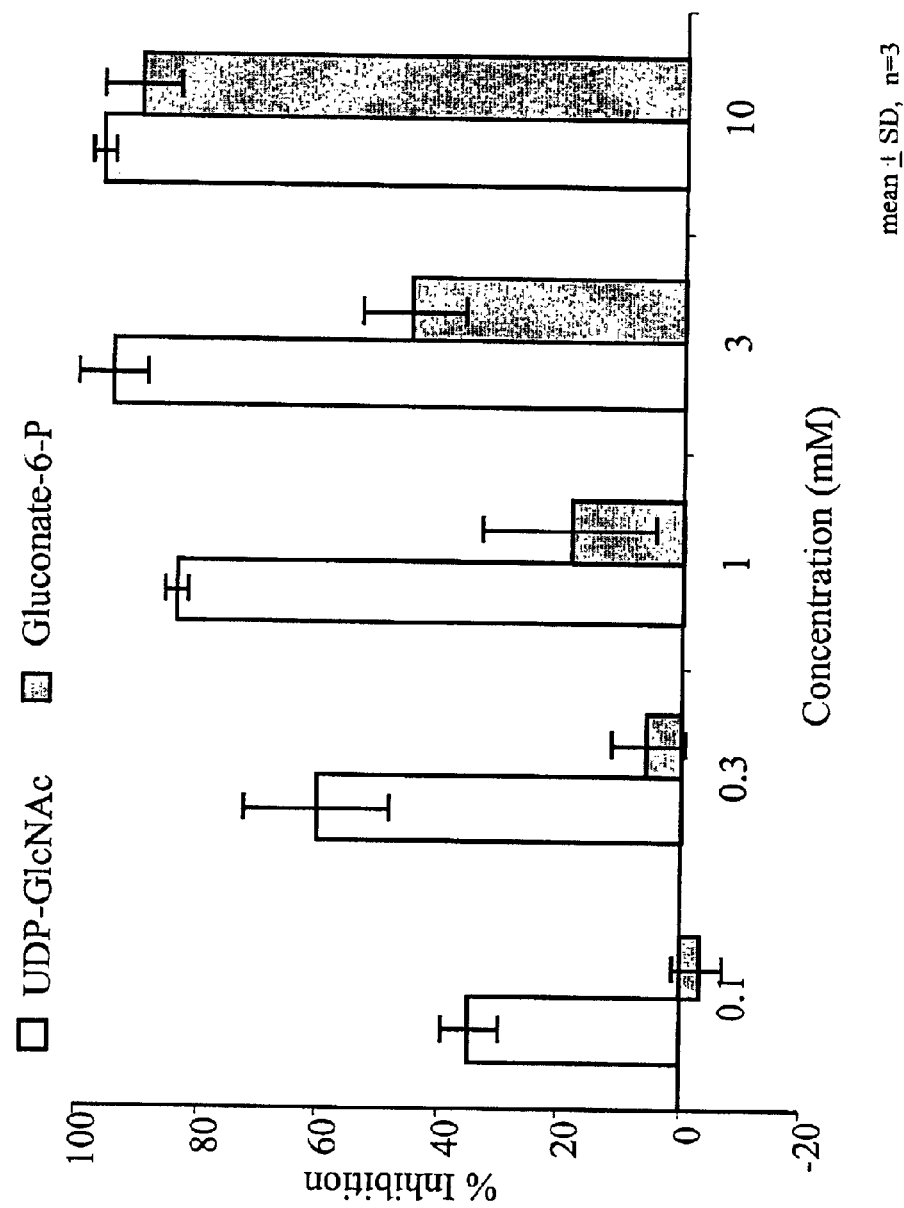
FIG. 5 shows that the addition of gluconate-6-phosphate and UDP-GlcNAc to crude A. fumigatus lysates inhibited the production of CoA in a dose dependent manner.

Phosphoglucose isomerase activity is competitively inhibited by gluconate-6-phosphate (Marchand et al., supra [1989]), while eukaryotic ketol-isomerases are feedback-inhibited by UDP-GlcNAc. Therefore, using the method described above, the effects of these two control inhibitors were investigated. The results of these assays are shown in FIG. 5. The results obtained using the assay described in Example 2, indicated that both gluconate-6-phosphate and UDP-GlcNAc inhibited the formation of CoA (GlcNAc-6-P) in a dose-dependent manner. Thus, the CoA formation assay can be used successfully to detect inhibition of fungal glucose metabolic reactions in vitro.

EXAMPLE 4

Screening Natural Product Extracts for the Ability to Inhibit Fungal Phosphoglucose Isomerase, Ketol-Isomerase and N-Acetyltransferase In this Example, the use of the colorimetric CoA (GlcNAc-6-P) formation assay, to identify inhibitors of fungal glucose utilization is described. Specifically, the screening of various natural product extracts is contemplated.

The extracts are obtained from a number of sources including: extremophile microorganism extracts from Montana Biotech (Belgrade, Mont.); marine macroorganism extracts from Harbor Branch Oceanographic Institution (Ft. Pierce, Fla.); and cynaobacteria and algae extracts from Aquaartis (France). In addition the mass screening of various extracts from other libraries is contemplated. These libraries include ethnobotanical extracts, extremophile extracts, marine macroorganism extracts, microorganism extracts and chemical compounds.

Extracts to be tested are placed in deep-well 96-well microtiter plates and dissolved in a suitable solvent (e.g., DMSO). An aliquot of the extract is added to wells of microtiter plates, followed by the addition of buffered substrates and crude or gel-filtered fungal cell lysates. After incubation, reactions are terminated by the addition of 50 μl of 6.4 M guanidine hydrochloride. Following addition of 50 μl of 200 μM DTNB to each well, the samples are incubated at room temperature for 10 minutes. The formation of CoA is then measured by photometrically ($OD_{412}$). Samples inhibiting the formation of CoA by greater than 50% are scored as positive and retested.

EXAMPLE 5

Screening Natural Product Extracts for Antifungal Activity

In this Example, the use of an agar diffusion assay to test positive samples (e.g., samples scored as "positive" in the colorimetric CoA(GlcNAc-6-P) formation assay of Example 4) for their ability to inhibit fungal growth is described.

Each positive sample from Example 4 is assessed for its ability to inhibit the growth of A. fumigatus (ATCC 16424) and C. Albicans (ATCC 90028). Two microliters of each sample are plated onto the surface of agar-solidified RPMI medium containing $1 \times 10^6$ conidia per ml. Amphotericin B and DMSO serve as positive and negative controls respectively. The diameter of each inhibitory zone is measured after incubation for 18–24 hours at 37° C. (A. fumigatus) or 35° C. (C. albicans). It is contemplated that compounds that inhibit one of the three enzymes whose activity is measured in the CoA(GlcNAc-6-P) formation assay also possess antifungal activity as measured in this agar diffusion assay.

EXAMPLE 6

Fractionate Extracts with Antifungal Activity

The samples that inhibit fungal glucose utilization are separated to about 70 fractions by reverse phase high performance liquid chromatography (HPLC). The separated fractions are evaporated and dissolved in DMSO. The antifungal activity is determined by the method described in Example 4. The active fractions are further separated by HPLC in order to obtain a pure compound.

EXAMPLE 7

Examine the Activity of Inhibitors Against Human Fungal Pathogens

Methods for testing the activity of the newly-identified glucose utilization inhibitors, against the fungi listed in Table 6, are provided. The NCCLS 27T microtiter broth assay (MycoLogics) is used to assess antifungal activity. In brief, each fungal strain except A. fumigatus is grown to mid-log phase, counted, and added to microtiter plates in RPMI 1640 medium at $1 \times 10^3$ cells/well. Various amounts of each inhibitor or vehicle (e.g., 0.1% DMSO) is added to each well in 2 μl, for a total well volume of 200 μl. The plates are incubated at 30° C. for 24 to 48 hours and the growth of fungi is then quantitated. For A. fumigatus, conidia are harvested from stock agar cultures and distributed to microtiter plates at $1 \times 10^4$ conidia/well. Fungal growth is measured after incubation at 32° C. for 48 hours with various amounts of each inhibitor or vehicle.

TABLE 6

Panel of Human Fungal Pathogens

| Microorganism | ATCC Number |
| --- | --- |
| C. albicans | 90028 |
| C. albicans | 10231 |
| C. albicans | 44203 |
| C. albicans | 32354 |
| C. albicans | 44806 |
| C. albicans | 76485 |
| C. albicans | 90234 |
| C. albicans | 90873 |
| C. glabrata | 48435 |
| C. tropicalis | 90874 |
| C. kuzei | 34135 |
| C. parapsilosis | 90018 |
| A. fumigatus | 16424 |
| C. neoformans | 36556 |

EXAMPLE 8

Determine the Toxicity of the Inhibitors to Human Cell Lines In Vitro

Suspensions of skhep-1 (liver-derived) cells, SW 839 (kidney-derived) cells, and A-427 (lung-derived) cells are diluted and added to 96 well microtiter plates at 5,000 to 40,000 cells/well based on the growth characteristics of each cell line. Each inhibitor is added in amounts in excess of that effective against C. albicans. Cell growth is quantitated after incubation for 48 hours at 37° C., in 5% $CO_2$ and 100% humidity. Toxicity is reported as the 50% growth inhibition concentration (GI50) according to the standard screening procedures set forth by the National Cancer Institute (See, Monks et al., J Natl Cancer Inst 83:757–66 [1991]; and http://dtp.nci.nih.gov/docs/compare/compare%5Fmethodology.html).

EXAMPLE 9

Determine the Toxicity of the Inhibitors to Mice In Vivo

The use of single and multiple dose protocols are contemplated for assessing the toxicity to mammals of the newly identified antifungal inhibitors. For the single administration protocol, the inhibitors are administered intravenously, intraperitoneally or subcutaneously to mice at doses ranging from 0 to 1000 mg/kg. The 50% lethal dose (LD50) is calculated based on the mortality rate observed seven days after inhibitor administration. For the multiple administration protocol, the inhibitors are administered intravenously, intraperitoneally or subcutaneously to mice once daily for seven consecutive days at doses ranging from 0 to 1000 mg/kg. The LD50 is calculated based on the mortality rate observed seven days after the final inhibitor administration.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in enzymology, medical microbiology or related fields are intended to be within the scope of the following claims.

What is claimed is:

1. A method for the detection of phosphoglucose isomerase, ketol-isomerase and acetyltransferase activities in a sample, comprising the steps of:
   a) providing:
      i) a sample suspected to contain phosphoglucose isomerase, ketol-isomerase and acetyltransferase activities,
      ii) glucose-6-phosphate,
      iii) glutamine,
      iv) acetyl coenzyme A, and
      v) 5,5'-dithiobis(2-nitrobenzoic acid);
   b) combining said sample, said glucose-6-phosphate, said glutamine, and said acetyl coenzyme A under conditions to yield reaction products comprising coenzyme A and N-acetylglucosamine-6-phosphate;
   c) inactivating said phosphoglucose isomerase, ketol-isomerase and acetyltransferase activities; and
   d) combining said reaction product comprising coenzyme A and 5,5'-dithiobis(2-nitrobenzoic acid) under conditions to yield a chromogenic reaction product comprising 2-nitro-thiobenzoate anion, wherein said chromogenic reaction product is indicative of phosphoglucose isomerase, ketol-isomerase and acetyltransferase activities.

2. The method of claim 1, wherein said sample comprises a lysate selected from the group consisting of crude cell lysates and gel filtered cell lysates.

3. The method of claim 2, wherein said lysate is a fungal cell lysate selected from the group consisting of Aspergillus cell lysates, Candida cell lysates, Cryptococcus cell lysates, Histoplasma cell lysates, Pneumocystis cell lysates, Rhizopus cell lysates, Saccharomyces cell lysates, and Schizosaccharomyces cell lysates.

4. The method of claim 1, wherein said sample comprises purified fungal enzymes selected from the group consisting of phosphoglucose isomerases, ketol-isomerases and acetyltransferases.

5. The method of claim 1, wherein said sample comprises recombinant fungal enzymes selected from the group consisting of phosphoglucose isomerases, ketol-isomerases and acetyltransferases.

6. A method for the detection of a compound having the ability to inhibit phosphoglucose isomerase, ketol-isomerase and/or acetyltransferase activities in a sample, comprising the steps of:
   a) providing:
      i) a sample suspected to contain phosphoglucose isomerase, ketol-isomerase and acetyltransferase activities,
      ii) glucose-6-phosphate,
      iii) glutamine,
      iv) acetyl coenzyme A,
      v) 5,5'-dithiobis(2-nitrobenzoic acid), and
      vi) a candidate compound;
   b) preparing a first and second reaction mixture, wherein said first reaction mixture comprises said sample, said glucose-6-phosphate, said glutamine, and said acetyl coenzyme A, and wherein said second reaction mixture comprises said sample, said glucose-6-phosphate, said glutamine, said acetyl coenzyme A and said candidate compound;
   c) incubating said first and second reaction mixtures under conditions of yield reaction products comprising coenzyme A and N-acetylglucosamine-6-phosphate;
   d) inactivating said phosphoglucose isomerase, ketol-isomerase and acetyltransferase activities;
   e) combining said first and second reaction mixtures with said 5,5'-dithiobis(2-nitrobenzoic acid) under conditions to yield a chromogenic reaction product comprising 2-nitro-thiobenzoiate anion; and
   f) comparing the quantity of said chromogenic reaction product in said first and second reaction mixtures.

7. The method of claim 6, further comprising step g) scoring said candidate compounds as positive for the ability to inhibit phosphoglucose isomerase, ketol-isomerase and/or acetyltransferase activities in a sample, when said second reaction mixture yields less than 50% of said chromogenic reaction product than said first reaction mixture.

8. The method of claim 6, wherein said sample comprises a lysate selected from the group consisting of crude cell lysates and gel filtered cell lysates.

9. The method of claim 8, wherein said lysate is a fungal cell lysate selected from the group consisting of Aspergillus cell lysates, Candida cull lysates, Cryptococcus cell lysates, Histoplasma cell lysates, Pneumocystis cell lysates, Rhizopus cell lysates, Saccharomyces cell lysates, and Schizosaccharomyces cell lysates.

10. The method of claim 6, wherein said sample comprises purified fungal enzymes selected from the group consisting of phosphoglucose isomerases, ketol-isomerases and acetyltransferases.

11. The method of claim 6, wherein said sample comprises recombinant fungal enzymes selected from the group consisting of phosphoglucose isomerases, ketol-isomerases and acetyltransferases.

12. The method of claim 6, wherein said candidate compound is present in an extract selected from the group consisting of extremophile extracts, marine macroorganism extracts, cyanobacterial extracts and algal extracts.

\* \* \* \* \*